(12) United States Patent
Machida et al.

(10) Patent No.: US 10,603,689 B2
(45) Date of Patent: Mar. 31, 2020

(54) ULTRASONIC TRANSDUCER, METHOD FOR MAKING SAME, ULTRASONIC TRANSDUCER ARRAY, AND ULTRASONIC TEST APPARATUS

(71) Applicant: Hitachi, Ltd., Tokyo (JP)

(72) Inventors: Shuntaro Machida, Tokyo (JP); Daisuke Ryuzaki, Tokyo (JP); Tatsuya Nagata, Tokyo (JP); Naoaki Yamashita, Tokyo (JP); Yuko Hanaoka, Tokyo (JP); Yasuhiro Yoshimura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 380 days.

(21) Appl. No.: 15/513,588

(22) PCT Filed: Apr. 21, 2015

(86) PCT No.: PCT/JP2015/062135
§ 371 (c)(1),
(2) Date: Mar. 23, 2017

(87) PCT Pub. No.: WO2016/047186
PCT Pub. Date: Mar. 31, 2016

(65) Prior Publication Data
US 2017/0291192 A1    Oct. 12, 2017

(30) Foreign Application Priority Data
Sep. 26, 2014  (JP) .................................. 2014-196805

(51) Int. Cl.
*B06B 1/06*    (2006.01)
*G01N 29/24*    (2006.01)
(Continued)

(52) U.S. Cl.
CPC .............. *B06B 1/06* (2013.01); *B06B 1/0292* (2013.01); *B06B 1/0607* (2013.01);
(Continued)

(58) Field of Classification Search
CPC ......... H01L 41/02; H01L 41/22; H01L 41/25; H01L 41/27
See application file for complete search history.

(56) References Cited

U.S. PATENT DOCUMENTS 6,320,239 B1    11/2001  Eccardt et al.
7,323,778 B2    1/2008   Shizuno
(Continued)

FOREIGN PATENT DOCUMENTS

JP    2004-165193 A    6/2004
JP    2009-207882 A    9/2009
(Continued)

OTHER PUBLICATIONS

International Preliminary Report on Patentability received in corresponding International Application No. PCT/JP2015/062135 dated Apr. 6, 2017.
(Continued)

*Primary Examiner* — Austin Murata
(74) *Attorney, Agent, or Firm* — Mattingly & Malur, PC

(57) ABSTRACT

A structure that prevents a substrate from being warped is provided on a region or a location other than a membrane that determines the characteristics of a CMUT. In a CMUT in a structure in which a first conductive layer and a second conductive layer are provided sandwiching a cavity on a substrate, for example, as a warpage prevention structure, a warpage prevention layer that prevents the substrate from being warped is provided between the substrate and the first conductive film. When the insulating film disposed between the cavity and the first conductive film and the insulating
(Continued)

film disposed between the cavity and the second conductive film are silicon oxide films, the warpage prevention layer includes a silicon nitride film.

5 Claims, 21 Drawing Sheets

(51) Int. Cl.
*G01N 29/04* (2006.01)
*B06B 1/02* (2006.01)
*H04R 31/00* (2006.01)
*H04R 19/00* (2006.01)
*A61B 8/00* (2006.01)

(52) U.S. Cl.
CPC ......... *B06B 1/0644* (2013.01); *G01N 29/043* (2013.01); *G01N 29/24* (2013.01); *G01N 29/2406* (2013.01); *A61B 8/4461* (2013.01); *A61B 8/4494* (2013.01); *G01N 2291/0232* (2013.01); *G01N 2291/106* (2013.01); *H04R 19/005* (2013.01); *H04R 31/00* (2013.01)

(56) References Cited

U.S. PATENT DOCUMENTS

| | | | |
|---|---|---|---|
| 7,982,369 B2 | 7/2011 | Ona et al. | |
| 2005/0230794 A1 | 10/2005 | Shizuno | |
| 2007/0222338 A1* | 9/2007 | Aono | B06B 1/0292 310/334 |
| 2009/0204001 A1 | 8/2009 | Ona et al. | |
| 2011/0115333 A1* | 5/2011 | Ezaki | B06B 1/0292 310/300 |
| 2013/0255388 A1 | 10/2013 | Takeuchi et al. | |

FOREIGN PATENT DOCUMENTS

| | | |
|---|---|---|
| JP | 2012-099847 A | 5/2012 |
| JP | 2013-150198 B2 | 8/2013 |
| JP | 2013-226391 A | 11/2013 |

OTHER PUBLICATIONS

International Search Report of PCT/JP2015/062135 dated Jun. 9, 2015.

* cited by examiner (a)

(b)

CURVATURE RADIUS R OF SUBSTRATE

201 SUBSTRATE

RADIUS r OF SUBSTRATE
WARPED AMOUNT C = R(1−cos(r/R(rad)))

WARPED AMOUNT C (a)

(b)

(a)

(b)

(a)

(b)

(a)

(b)

(a)

(b)

(a)

(b)

(a)

(b)

(a)

(b)

(a)

(b)

(a)

(b)

ULTRASONIC TRANSDUCER, METHOD FOR MAKING SAME, ULTRASONIC TRANSDUCER ARRAY, AND ULTRASONIC TEST APPARATUS

TECHNICAL FIELD

The present invention relates to a technique of manufacturing an ultrasound transducer, and more specifically to the structure of an ultrasound transducer manufactured by MEMS (Micro Electro Mechanical System) techniques and an effective technique applied to a manufacturing method therefor.

BACKGROUND ART

The ultrasound transducers are used for various use applications such as ultrasonic diagnostic apparatuses that examine and diagnose human bodies in a noninvasive manner by transmitting and receiving ultrasonic waves and ultrasonic examination apparatuses that inspect cracks and the like opened in buildings.

Previously existing ultrasound transducers use vibrations of a piezoelectric element. With the advancement of the MEMS techniques in these years, a capacitive micromachined ultrasonic transducer (CMUT) is developed, in which a diaphragm is fabricated on a silicon substrate (Patent Literature 1).

The CMUT has a structure in which an upper electrode and a lower electrode are disposed sandwiching a cavity. The CMUT has advantages such as a wide frequency band of usable ultrasonic waves, i.e. high sensitivity, micromachinable structures because of the fabrication using LSI techniques, and others, compared with ultrasound transducers using previously existing piezoelectric elements. The CMUT is also put to practical use in the ultrasonic examination apparatuses described above and other devices (Patent Literature 2 and Patent Literature 3).

Patent Literature 2 discloses a structure in which a lower electrode and an upper electrode facing a cavity are each covered with an insulating film. Patent Literature 3 discloses a CMUT having a structure in which an upper electrode and a lower electrode are covered with an insulating layer formed of a silicon nitride film for electrically insulating a silicon substrate from the electrodes of the CMUT except a cavity.

A direct voltage and an alternating voltage are applied in superposition to the upper and lower electrodes disposed sandwiching the cavity to generate electrostatic force between the upper and lower electrodes, and a membrane formed of films disposed above the cavity is vibrated at a frequency of the alternating voltage. Thus, this implements the transmission of ultrasonic waves by the CMUT. After receiving the pressure of ultrasonic waves, the membrane is vibrated to change the distance between the upper and lower electrodes, and a change in this distance is detected as a change in electrostatic capacitance. Thus, this implements the reception of ultrasonic waves by the CMUT.

From the principle of the transmission and reception of ultrasonic waves by the CMUT as described above, it is important in the design of the CMUT to appropriately determine the distance between the upper and lower electrodes. The distance between the upper and lower electrodes is determined by the thickness of the cavity and the thicknesses of the insulating films provided sandwiching the cavity. In order to maintain the thickness of the cavity, it is important to keep the shape of the membrane flat, i.e. to prevent the membrane from being deformed to cause a change in the thickness of the cavity. To this end, in the design of the previously existing CMUT (e.g. Patent Literature 2), the layer configuration of the membrane is devised, such as disposing a silicon nitride insulating film of low tensile stress on an insulating layer directly above the cavity.

CITATION LIST

Patent Literatures

Patent Literature 1: U.S. Pat. No. 6,320,239B1
Patent Literature 2: Japanese Unexamined Patent Application Publication No. 2013-150198
Patent Literature 3: Japanese Unexamined Patent Application Publication No. 2009-207882

SUMMARY OF INVENTION

Technical Problem

In the MEMS techniques, a CMUT is manufactured, in which layers configuring a CMUT are in turn patterned on a substrate for forming films. In forming the CMUT, a cavity is formed by a method in which first, a sacrificial layer is formed, an insulating film and other films are formed on the sacrificial layer, and then the sacrificial layer is etched for removal through an etching hole.

In such manufacturing process steps, a substrate is sometimes warped because of the residual stress of films formed on the substrate. When the substrate is greatly warped, problems arise in that the substrate fails to be chucked to a stage in a fabrication system, for example, in the manufacturing process steps of the CMUT. Thus, processing fails to proceed. In the process step of cutting a wafer into chips and assembling the chips into an ultrasound probe, a warped wafer or warped chips probably cause the wafer or the chips to be broken or cause other failures.

The warpage of the substrate may be reduced by controlling the properties of films stacked on the substrate. However, as described above, films such as insulating films formed on the substrate are designed to optimize the characteristics of the CMUT (the drive voltage or reception sensitivity). Thus, it is not preferable to change the film configuration for preventing the substrate from being warped.

Therefore, the present invention is to provide a structure and a manufacturing method therefor that can reduce the warpage of a substrate formed with a CMUT without affecting an optimized film configuration that maintains the characteristics of the CMUT and prevents a membrane from being distorted.

Solution to Problem

The present invention is characterized in that a structure that prevents a substrate from being warped is provided on a region or a location other than a membrane that determines the characteristics of a CMUT. The warpage prevention structure roughly has two aspects.

One aspect is an aspect in which a layer that prevents a substrate from being warped is provided on the lower side of a lower electrode of a CMUT, i.e. between the lower electrode and the substrate. The other aspect is an aspect in which a layer that prevents the substrate from being warped is provided on a region other than a region of the substrate on which the CMUT is provided. These two aspects can be combined.

Advantageous Effects of Invention

According to the present invention, a substrate can be prevented from being warped, without blocking the characteristics of an ultrasound transducer. Accordingly, in manufacture of an ultrasound transducer or in assembling an ultrasound probe, problems caused by the warpage of a substrate can be solved.

DESCRIPTION OF EMBODIMENTS

Figure 1:
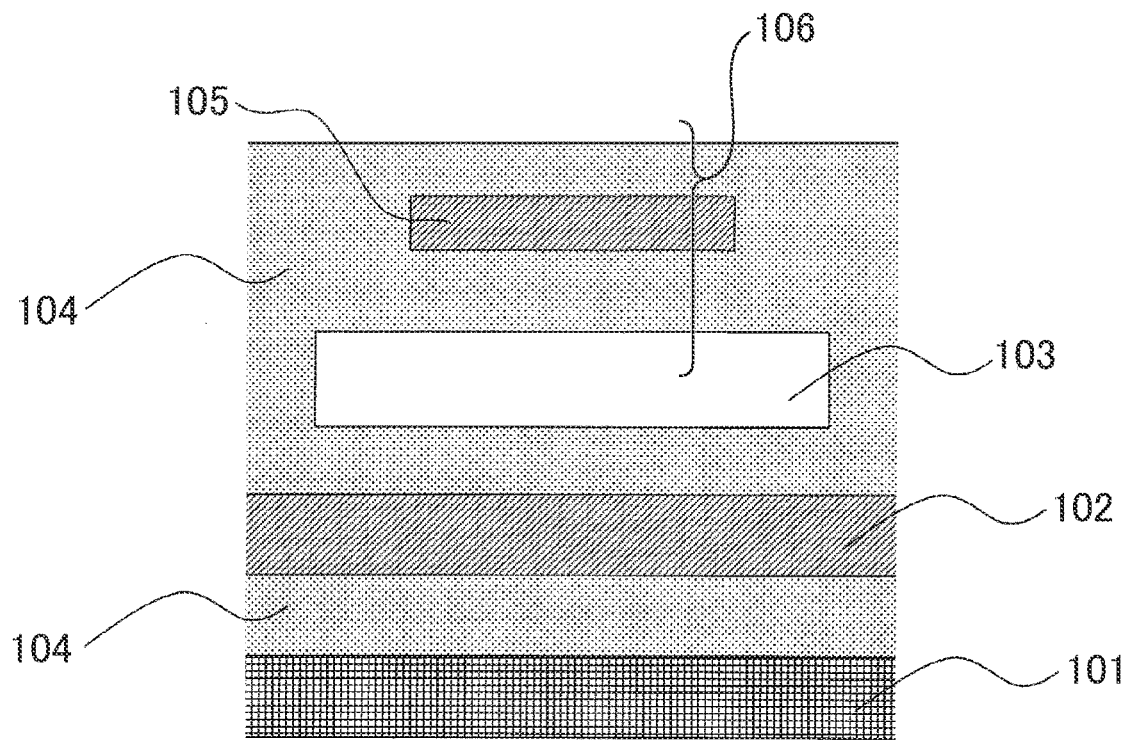
FIG. 1 is a cross sectional view of the structure of a typical CMUT.

In the following, embodiments of an ultrasound transducer, a manufacturing method for an ultrasound transducer, and an ultrasonic examination apparatus according to the present invention will be described with reference to the drawings.

Note that, in all the drawings for explaining the embodiments below, in principle, the same members are designated the same reference numerals and signs, and the repeated description is omitted. In the embodiments below, for convenience, the embodiments will be described as they are split into a plurality of sections or examples as necessary. However, they have some relations, in which one is a part of or all of the exemplary modifications, details, supplementary explanations, and the like of the other, unless otherwise specified.

In the embodiments below, in the case where the numbers of elements, for example, are referred (including the numbers of items, numeric values, quantities, ranges, and other parameters), these parameters are not limited to the specific numbers, which may have values equal to or greater or less than these specific numbers, unless otherwise specified or unless the specific numbers are clearly limited to specific numbers in principle. Moreover, in the embodiments below, it goes without saying that the components (also including element steps and the like) are not necessarily required, unless otherwise specified or unless they are clearly required in principle.

Similarly, in the embodiments below, when the shapes and positional relationship of the components, for example, are referred, substantially resemble ones or ones similar to the shapes and the like are included, unless otherwise specified or unless they are not clearly similar in principle. This is also applied to the numeric values and the ranges. Note that, for easy understanding, even plan views are sometimes hatched.

First Embodiment

First, an ultrasound transducer according to the present invention will be described with reference to an embodiment.

An ultrasound transducer according to the embodiment includes: a substrate; a first conductive film formed on the substrate; a first insulating film and a second insulating film formed on the first conductive film; a cavity provided between the first insulating film and the second insulating film; a second conductive film formed on the second insulating film; and a third insulating film covering the second conductive film. In the ultrasound transducer, a warpage prevention layer that prevents the substrate from being warped is provided between the substrate and the first conductive film.

In the ultrasound transducer according to the embodiment, when the substrate side is defined as the lower side and the third insulating film side is defined as the upper side, the warpage prevention layer includes a film formed of a material that generates stress in a direction in which the residual stress of a membrane configured of layers on the upper side of the first insulating film is cancelled.

The ultrasound transducer according to the embodiment is a so-called CMUT formed on the substrate by MEMS techniques, which may be a single element, or may be a CMUT array or a CMUT chip in which a large number of CMUT elements are disposed (in the following, a CMUT chip is a general term for the CMUT array and the CMUT chip).

In the following, the ultrasound transducer according to the embodiment will be described in detail as a single CMUT element taken as an example.

First Example

An ultrasound transducer according to this example is characterized in that a layer having tensile stress is provided as a warpage prevention layer between a substrate and a first conductive film configuring a CMUT.

First, the structure of a typical CMUT will be described. As illustrated in a cross sectional view of FIG. 1, in a CMUT, a lower electrode 102 is formed on a substrate 101 through an insulating film 104, and a cavity 103 is formed being surrounded by an insulating film 104 on the lower electrode 102. An upper electrode 105 is formed at a location overlapped with the cavity 103 above the cavity 103. A membrane 106 to be vibrated is configured of the insulating film 104 and the upper electrode 105 above the cavity 103. When a direct voltage and an alternating voltage are superposed between the upper electrode 105 and the lower electrode 102, electrostatic force acts between the upper electrode 105 and the lower electrode 102, and the membrane 106 is vibrated at the frequency of the applied alternating voltage. Thus, ultrasonic waves are transmitted. Conversely, in reception, the membrane 106 is vibrated by the pressure of ultrasonic waves reached on the surface of the membrane 106. Thus, this causes a change in the distance between the upper electrode 105 and the lower electrode 102, allowing the ultrasonic waves to be detected as a change in electrostatic capacitance.

The ultrasound transducer according to the example has a basic structure similar to the structure of the CMUT described above. However, the ultrasound transducer according to the example is characterized in that the insulating film 104 between the substrate 101 and the lower electrode (the first conductive film) 102 is a film (a warpage prevention layer) that prevents warpage generated on the substrate 101 due to the residual stress of the layers above the lower electrode 102.

In the following, referring to FIG. 2 and FIG. 3, the detail of the ultrasound transducer according to the example will be described.

Figure 2:
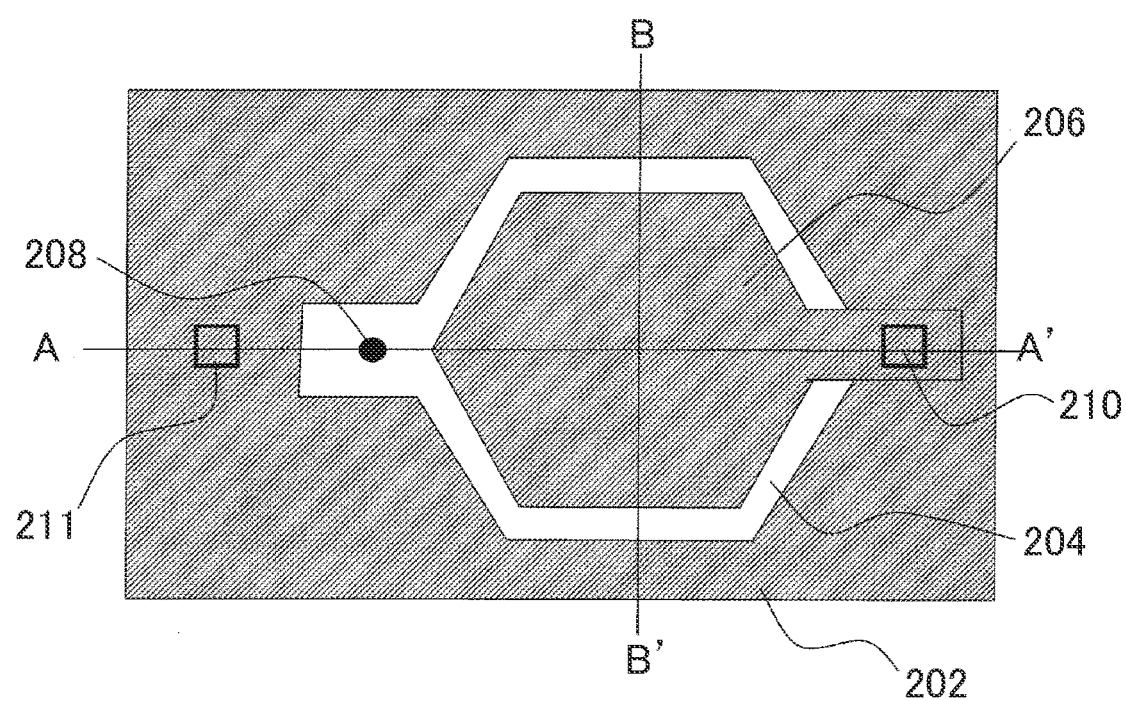
FIG. 2 is a diagram of the relationship of a first conductive film, a cavity, and a second conductive film of an ultrasound transducer according to a first embodiment when viewed from the top face.

FIG. 2 is a diagram of the positional relationship of a lower electrode (a first conductive film) 202, a cavity 204, and an upper electrode (a second conductive film) 203 when the ultrasound transducer according to the example is viewed from the top face (the face on the opposite side of a substrate). The upper electrode 206 has a shape when viewed from the top face almost the same as the shape of the cavity 204. The upper electrode 206 is apart from the lower electrode 202, and opposed to the lower electrode 202 as the cavity 204 is located between the upper electrode 206 and the lower electrode 202. The electrostatic capacitance of this transducer is determined by the overlapped area of the lower electrode 202 located on the lower side of the cavity 204 with the upper electrode 206 located on the upper side of the cavity 204.

Note that, in FIG. 2, the cavity 204 and the upper electrode 206 have a hexagonal shape when viewed from the top face of the substrate. However, the shape is not limited to this shape. For example, a circular shape and a rectangular shape are possible.

Figure 3:
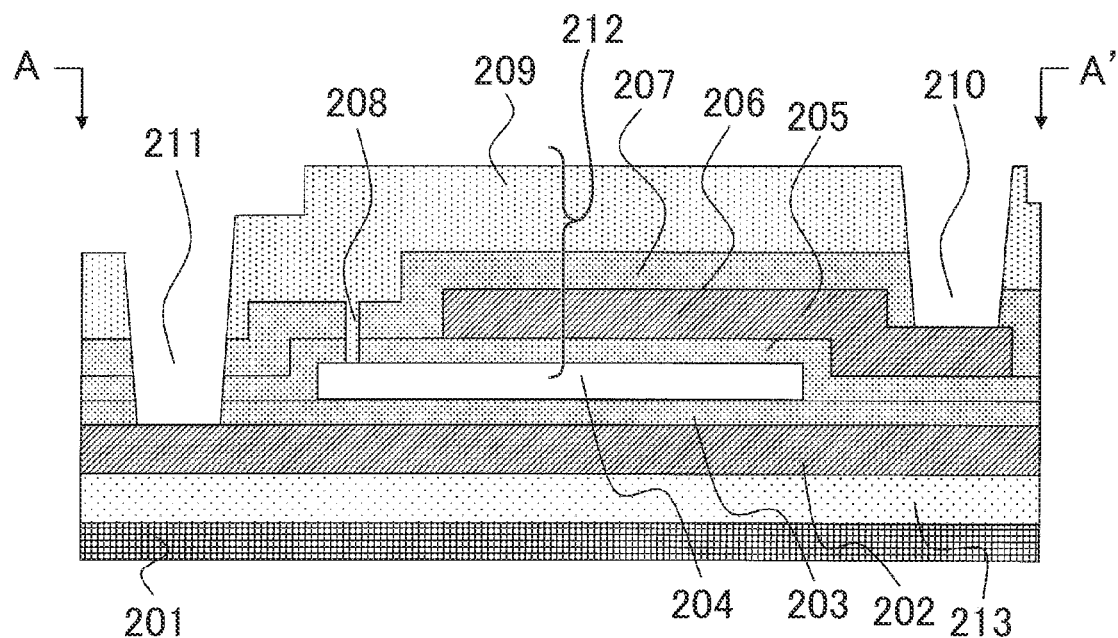
FIG. 3 shows diagrams of the ultrasound transducer according to the first embodiment (a first example); (a) is a cross sectional view taken along line A-A' in FIG. 2, and (b) is a cross sectional view taken along line B-B'.
Figure 3:
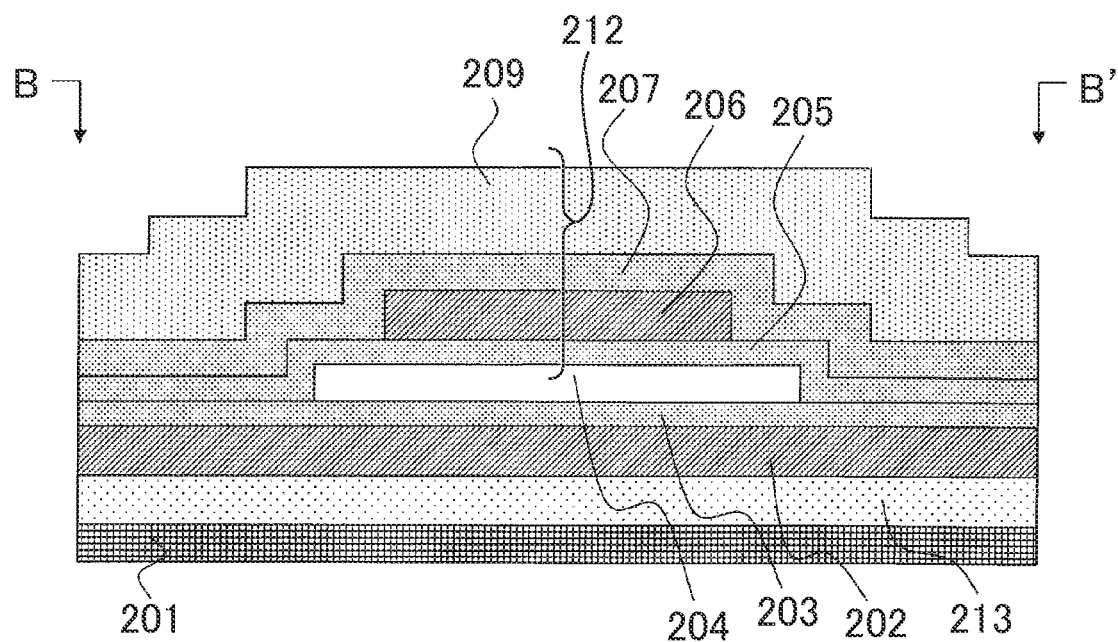

As illustrated in FIG. 3 (*a*) that is a cross sectional view taken along line A-A' in FIG. 2 and FIG. 3 (*b*) that is a cross sectional view taken along line B-B' in FIG. 2, the lower electrode 202 is provided on a substrate 201 through a warpage prevention film 213. On the lower electrode 202, the first insulating film 203, a second insulating film 205, the upper electrode 206, a third insulating film 207, and a protection insulating film 209 are stacked. Some or all of the insulating films 203, 205, 207, and 209 are appropriately collectively referred to as the insulating film. Pad openings 211 and 210 penetrating through the insulating films are provided to externally supply voltages to the lower electrode 202 and the upper electrode 206.

The cavity 204 is surrounded by the insulating films (the first insulating film 203 and the second insulating film 205). The layers located on the upper side of the cavity 204, i.e. the second insulating layer 205, the upper electrode 206, the third insulating film 207, and the protection insulating film 209 configure a membrane 212 that is vibrated when an the alternating voltage is applied across the lower electrode 202 and the upper electrode 206.

The thicknesses of the insulating films 203 and 205 sandwiched between the electrodes and the thickness of the cavity 204, which determine the distance between the upper and lower electrodes, are determined suitable for the drive voltage or size of the CMUT. The thicknesses are appropriately controlled for securing the stable operation of the CMUT. Sufficient accuracy of the thicknesses of the insulating films can be achieved by controlling the thicknesses in the processes of forming the insulating films in manufacturing the CMUT. The thickness of the cavity 204 is initially determined by the thickness of the sacrificial layer provided for forming the cavity 204 in the manufacturing process steps of the CMUT described later. However, in order to further reduce the deformation of the membrane 212, the membrane 212 is designed so that the residual stresses and thicknesses of the insulating films 205, 207, and 209 above the cavity 212 and the upper electrode 105 are adjusted to keep the shape of the membrane flat. For example, as the insulating films 205, 207, and 209, materials having different residual stresses are combined to adjust the stresses.

As the insulating films 203, 205, and 207 in contact with the electrodes, it is preferable to select materials having charge trapping sites as small as possible in the films. This is the reason that in the case where many charge trapping sites are included, leakage currents through the charge trapping sites are increased to drop the applied voltage is reduced, causing no stable operation to be secured.

Examples of materials and film thicknesses taking into account of the characteristics of the CMUT described above are shown.

First, examples of the materials of the electrode include alloys of titanium, titanium tungsten, and titanium nitride, and aluminum alloys. Single layer films or film stacks of these materials can be used. As a film stack, for example, a film stack having an alnimium alloy film sandwiched between titanium nitride films is preferable. The materials of the upper electrode 206 and the lower electrode 202 may be the same or different materials.

Although depending on the thicknesses and materials of the insulating films provided on both sides of the upper electrode 206, the thickness of the upper electrode 206 is about 500 nm, for example. The lower electrode 202 is not a film configuring the membrane 212, and the degree of freedom of the thickness is greater than the thickness of the upper electrode 206. Although the thickness is not limited specifically, the thickness is in a range of about 500 to 1,000 nm, for example.

The materials of the insulating films include silicon nitride and silicon oxide. In these materials, as the insulating films 203, 205, and 207 in contact with the lower electrode 202 and the upper electrode 206, silicon oxide having a few charge trapping sites is preferable. Although a silicon oxide film generates compressive stress, the silicon oxide film has a few charge trapping sites. Thus, even though the silicon oxide film has a relatively thin film thickness, the silicon oxide film can reduce leakage currents, and can prevent a voltage applied across the electrodes from being dropped and unstable operation caused by this drop.

Although the thicknesses of the insulating films 203 and 205 are not limited specifically, the thicknesses of the insulating films 203 and 205 can be in a range of about 100 to 300 nm. The thickness of the insulating film 207 can be in a range of about 300 to 1,000 nm.

The protection insulating film 209 provided on the insulating film 207 buries an etching hole 208 for etching the sacrificial layer to be the cavity 104 and seals the cavity 104, and is provided as the protective film of the CMUT. The insulating film 209 configures the membrane 212 together with the insulating films 205 and 207, and determines the residual stress of the membrane 212. Thus, in the case where the insulating films 205 and 207 are made of silicon oxide films that generate compressive stress, the insulating films 205 and 207 are preferably films having tensile stress. Specifically, a silicon nitride film is preferably used. The thickness of the protection insulating film 209 has to be a film thickness that sufficiently buries the etching hole 208, seals the cavity 104, and secures the flatness of the membrane 212. The thickness can be in a range of about 500 to 1500 nm, for example.

Next, materials on the lower side of the lower electrode 202 will be described.

The substrate 201 is a semiconductor substrate made of silicon, glass, or the like, and is not limited specifically, which only has to have a sufficient thickness for the support plate of the CMUT elements. For example, in the case of a silicon substrate in a diameter of eight inches, the thickness is 725 μm.

Figure 4:
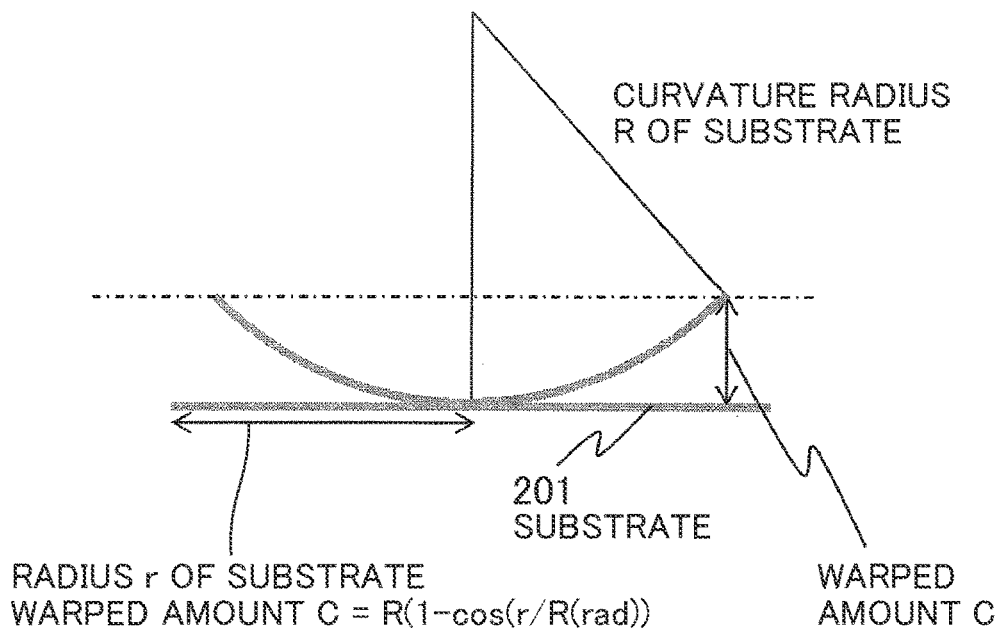
FIG. 4 is a diagram for explaining the occurrence of the warpage of the substrate of a CMUT and the warped amount.

The warpage prevention film 213 is a layer for preventing the substrate 201 from being deformed due to the stress of the layers above the lower electrode 202 as described above. For the warpage prevention film 213, a suitable material is selected taking into account of the residual stress of the layers above the lower electrode 202. In the case where silicon oxide films are used as the insulating layers 205 and 207 configuring the membrane 212 as described above, the silicon oxide film typically has compressive stress, which is the deforming stress that causes both ends of the substrate 201 to be warped upwardly as illustrated in FIG. 4. To such deforming stress, materials having tensile stress are preferable, and specifically a silicon nitride film is preferable.

Conversely, in the case where the residual stress of the films above the lower electrode 202 is the stress that causes deformation on the substrate in reverse to the deformation illustrated in FIG. 4, materials having compressive stress, i.e. a silicon oxide film is possibly used, for example. However, from the viewpoint that reduces leakage currents in the CMUT and secures the stability of operation, the most preferable combination is a combination using silicon oxide films as the insulating films 203, 205, and 207 and a silicon nitride film as the warpage prevention film 213.

Note that, in the CMUT disclosed in Patent Literature 3, a silicon nitride film is provided between the substrate and the lower electrode. However, in this CMUT, the other insulating layers are formed of the same material, and the silicon nitride film provided between the substrate and the lower electrode does not function as the warpage prevention layer of the substrate.

Here, the stress of the thin film formed on the substrate 201 can be written by Equation (1) below.

[Equation 1]

$$\sigma_f = \frac{E_s t_s^2}{(1-v_s)6t_f}\left(\frac{1}{R_1} - \frac{1}{R_0}\right) \quad (1)$$

In Equation 1, $\sigma_f$ is the stress of the thin film, $t_f$ is the thickness of the thin film, $E_s$ is the modulus of elasticity of the substrate, $t_s$ is the thickness of the substrate, $v_s$ is the Poisson's ratio of the substrate, $R_1$ is the curvature radius of the substrate when the thin film is formed, and $R_c$ is the curvature radius of the substrate before the thin film is formed. Here, in the case where $R_1$ is set to a positive value without taking into account of the orientation of warpage, a stress $\sigma_f$ of the thin film is a value whose symbol is different depending on tensile stress or compressive stress.

The curvature radius of the substrate $R_1$ when the thin film is formed is expressed by Equation (2) based on Equation (1).

[Equation 2]

$$\frac{1}{R_1} = \frac{6t_f(1-v_s)\sigma_f}{E_s t_s^2} + \frac{1}{R_0} \quad (2)$$

If the warpage of the substrate before the thin film is formed is very small and the curvature radius is infinite, Equation (2) is written to Equation (3).

[Equation 3]

$$R_1 = \frac{E_s t_s^2}{6t_f \sigma_f (1-v_s)} \quad (3)$$

In Equation (3), the modulus of elasticity and the thickness of the substrate, the thickness of the thin film, and the stress can be found by separately measuring them. Thus, from the curvature radius R of a substrate and the radius r of the substrate (in the case of a circular substrate), as illustrated in FIG. 4, a warped amount C of the substrate after the thin film is formed can be calculated. In other words, the warped amount C=R (1−cos (r/R)). Note that, for easily understanding the description, FIG. 4 exaggeratedly shows warpage, which is not a real warped amount of the substrate.

In the case where a plurality of thin films is stacked on the substrate, as illustrated in Equation (4), as first order approximation, the sum of the reciprocals of the curvature radii in forming the films on the substrate is the sum of the reciprocals of the curvature radii of the substrate on which the thin films are stacked.

[Equation 4]

$$\frac{1}{R_{multi-layer}} = \frac{1}{R_1} + \frac{1}{R_2} + \frac{1}{R_3} + \ldots \quad (4)$$

As described above, the warped amount of the substrate caused by the thin film or the stacked thin films is found. Thus, it is revealed that the warped amount can be reduced by combining materials whose symbols of the stress in Equation (1) are opposite and the warped amounts to be generated are the same.

Figure 5:
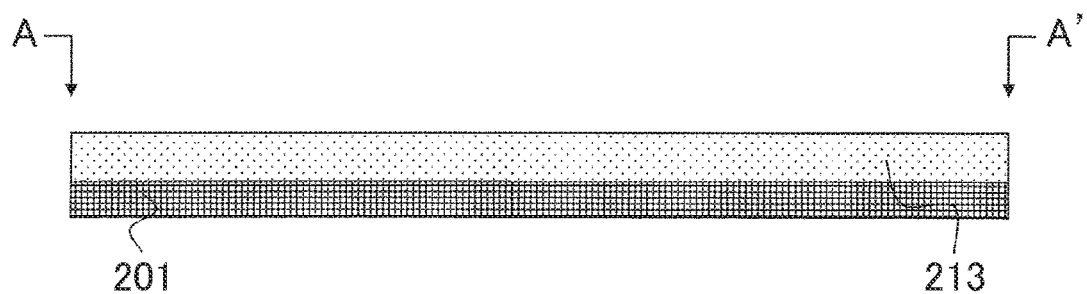
FIGS. 5 (a) and (b) are diagrams of a first process of a manufacturing method for the ultrasound transducer according to the first embodiment.
Figure 5:
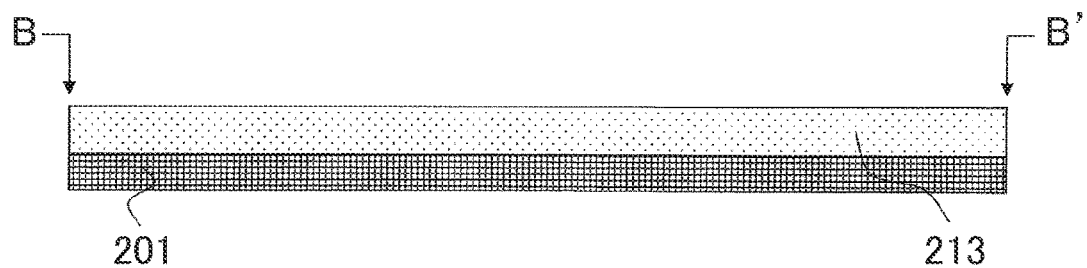

Next, based on the structure of the ultrasound transducer, referring to FIGS. 5 to 13, an exemplary manufacturing method for a CMUT will be described. FIGS. 5 a) to 13 (a) are cross sections in the direction taken along line A-A' in FIG. 2. FIGS. 5 (b) to 13 (b) are cross sections in the direction taken along line B-B' in FIG. 2.

First, as illustrated in FIGS. 5 (a) and (b), on the semiconductor substrate 201, the warpage prevention film 213 made of a silicon nitride film is formed in a thickness of 200 nm by low-pressure CVD (Chemical Vapor Deposition). At this time, the stress of the silicon nitride film is a tensile stress of about 2 GPa. Subsequently, on the warpage prevention film 213, a titanium nitride film, an aluminum alloy film, and a titanium nitride film are stacked in thicknesses of 100 nm, 600 nm, and 100 nm, respectively, by sputtering. These films are then patterned by techniques of photolithography and dry etching, and the lower electrode 202 is formed (FIGS. 6 (a) and (b)).

Figure 7:
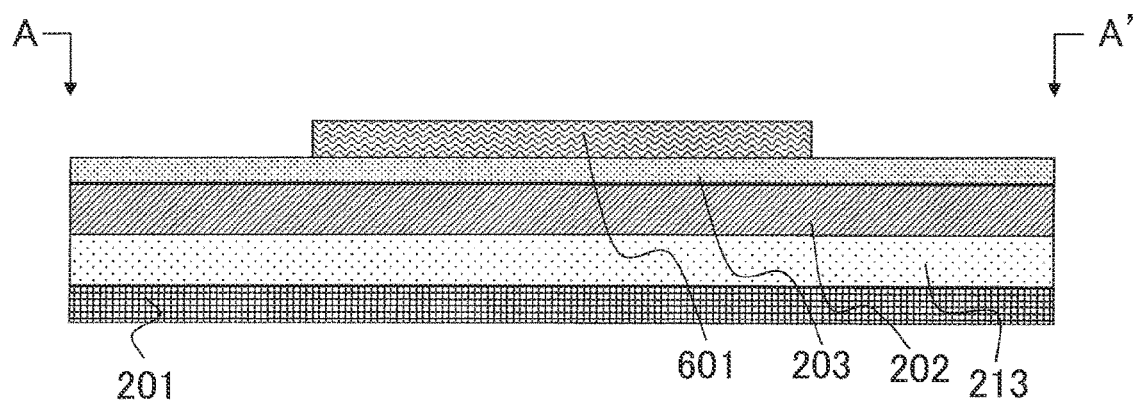
FIGS. 7 (a) and (b) are diagrams of a third process of the manufacturing method for the ultrasound transducer according to the first embodiment.
Figure 7:
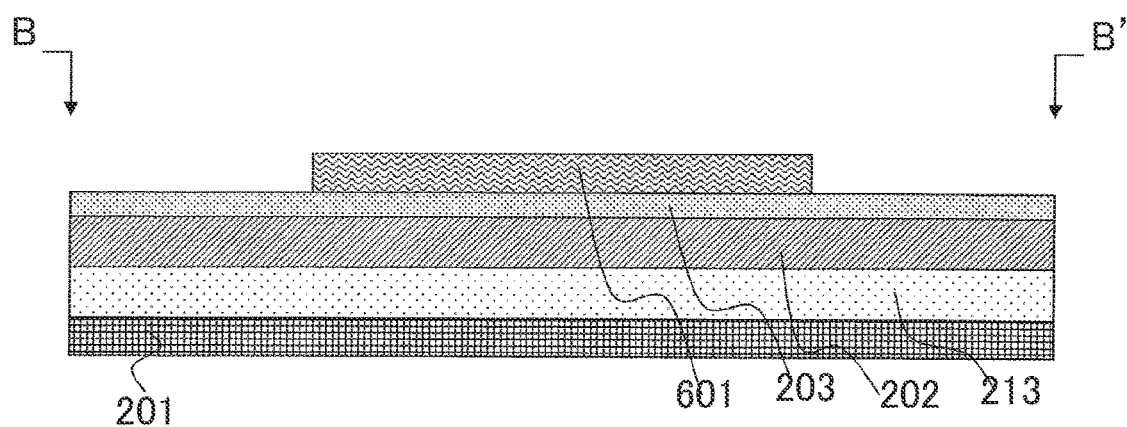

Subsequently, as illustrated in FIGS. 7 (a) and (b), on the lower electrode 202, the insulating film 203 made of a silicon oxide film is formed in a thickness of 100 nm by plasma CVD. After that, on the top face of the insulating film 203, a polysilicon film is formed in a thickness of 100 nm by plasma CVD, the polysilicon film is patterned by techniques of photolithography and dry etching, and then the sacrificial layer 601 made of a polysilicon film is formed on the insulating film 203. The sacrificial layer 601 is to be a cavity by processes later.

Figure 8:
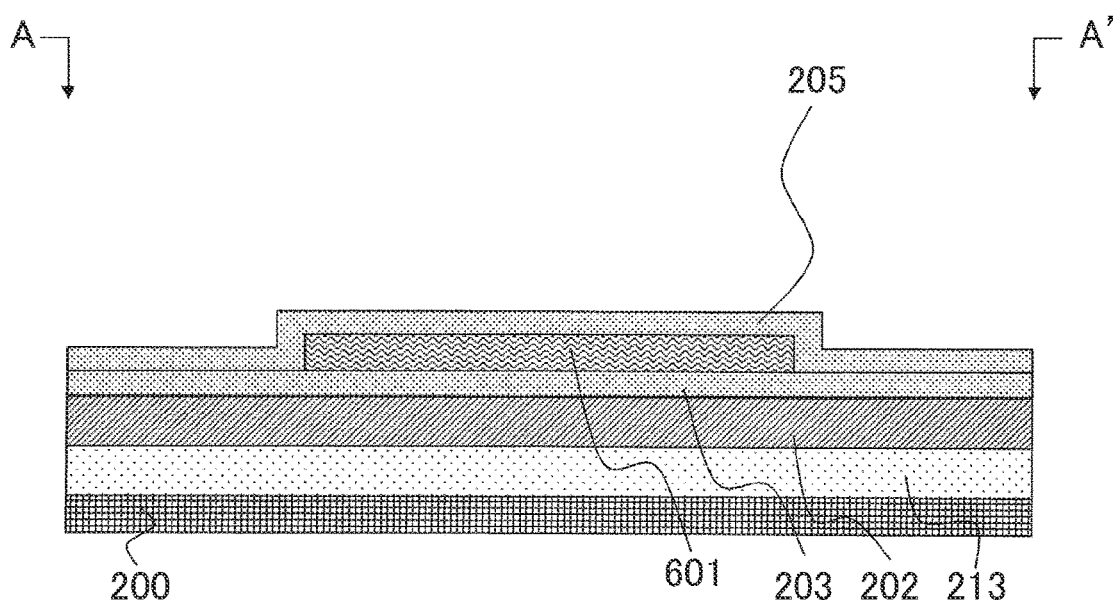
FIGS. 8 (a) and (b) are diagrams of a fourth process of the manufacturing method for the ultrasound transducer according to the first embodiment.
Figure 8:
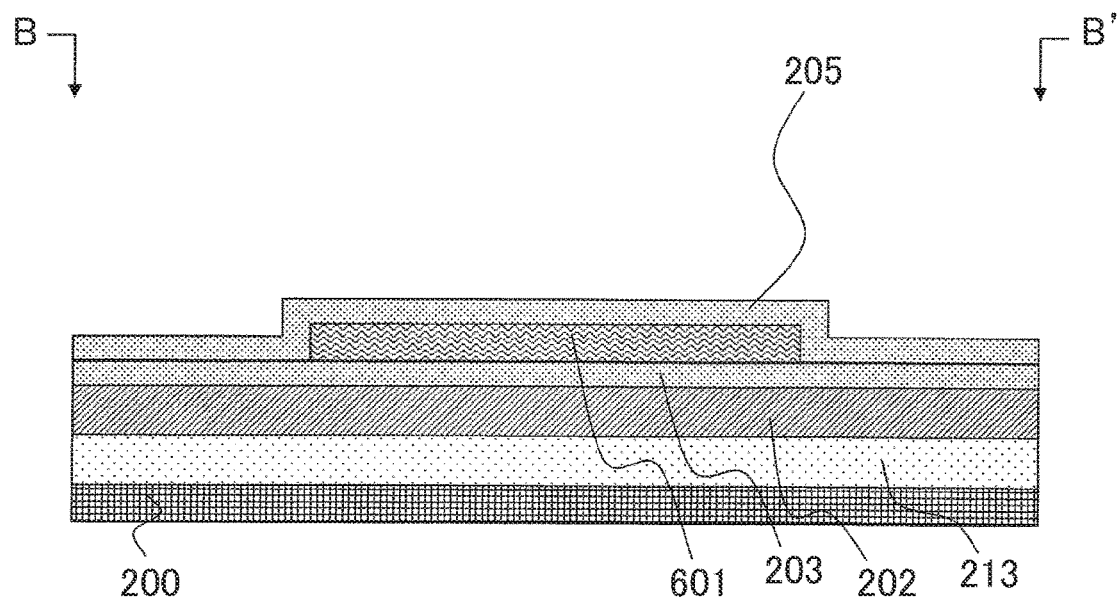
Figure 9:
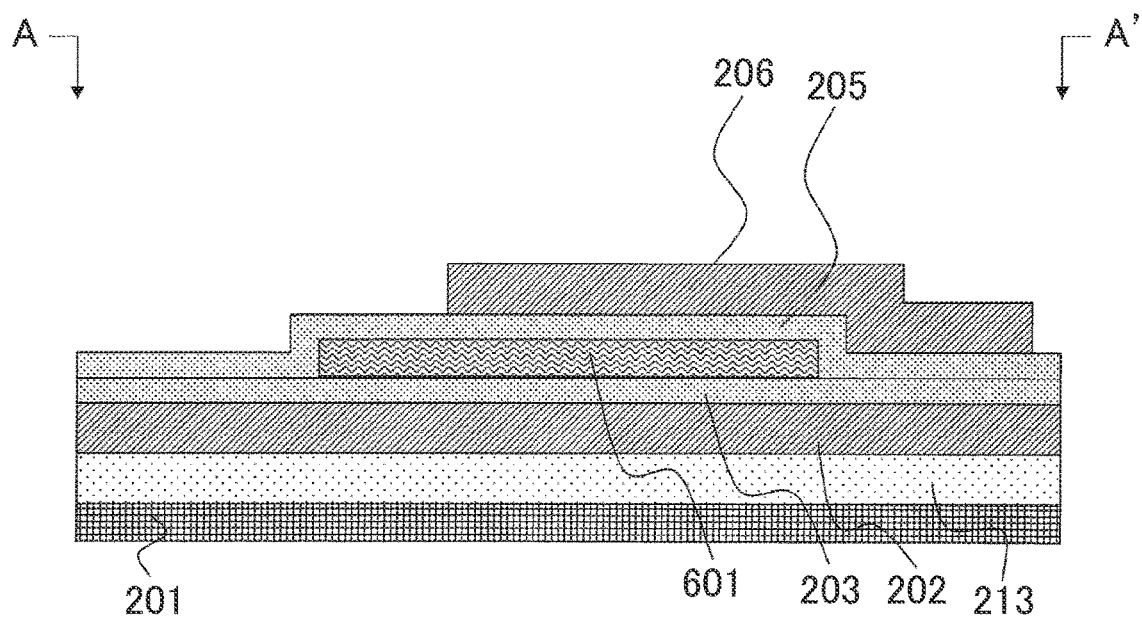
FIGS. 9 (a) and (b) are diagrams of a fifth process of the manufacturing method for the ultrasound transducer according to the first embodiment.
Figure 9:
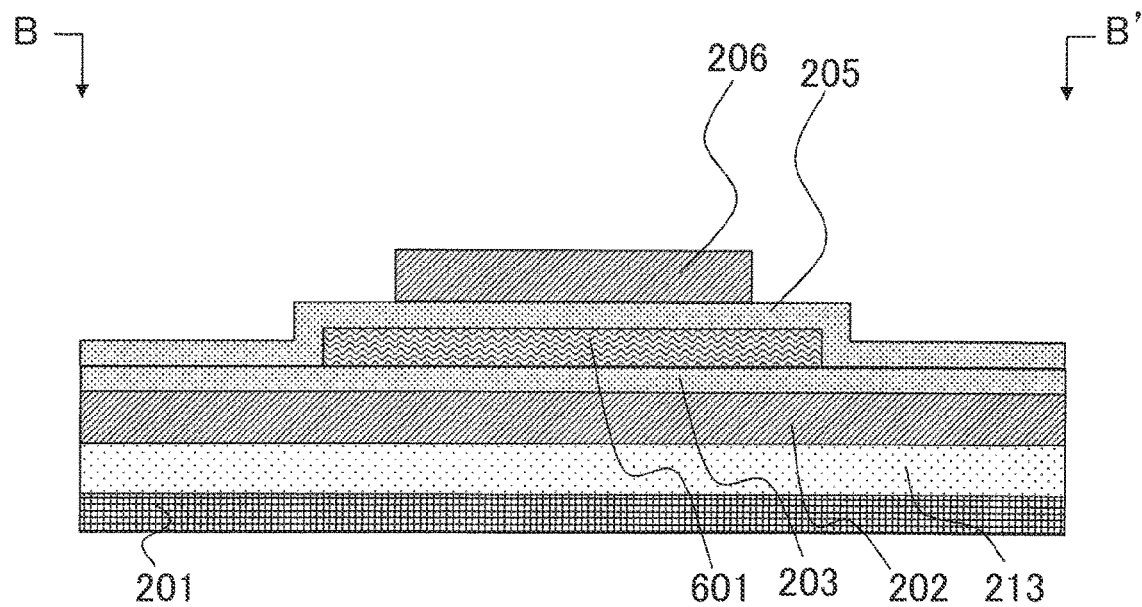

Subsequently, the insulating film 205 made of a silicon oxide film is formed in a thickness of 100 nm by plasma CVD so as to cover the sacrificial layer 601 and the insulating film 203 (FIGS. 8 (a) and (b)). Subsequently, in order to form the upper electrode 206 of the CMUT, a film stack of a titanium nitride film, an aluminum alloy film, and a titanium nitride film is formed in thicknesses of 50 nm, 300 nm, and 50 nm, respectively, by sputtering. The upper electrode 206 is then formed by techniques of photolithography and dry etching (FIGS. 9 (a) and (b)).

Figure 10:
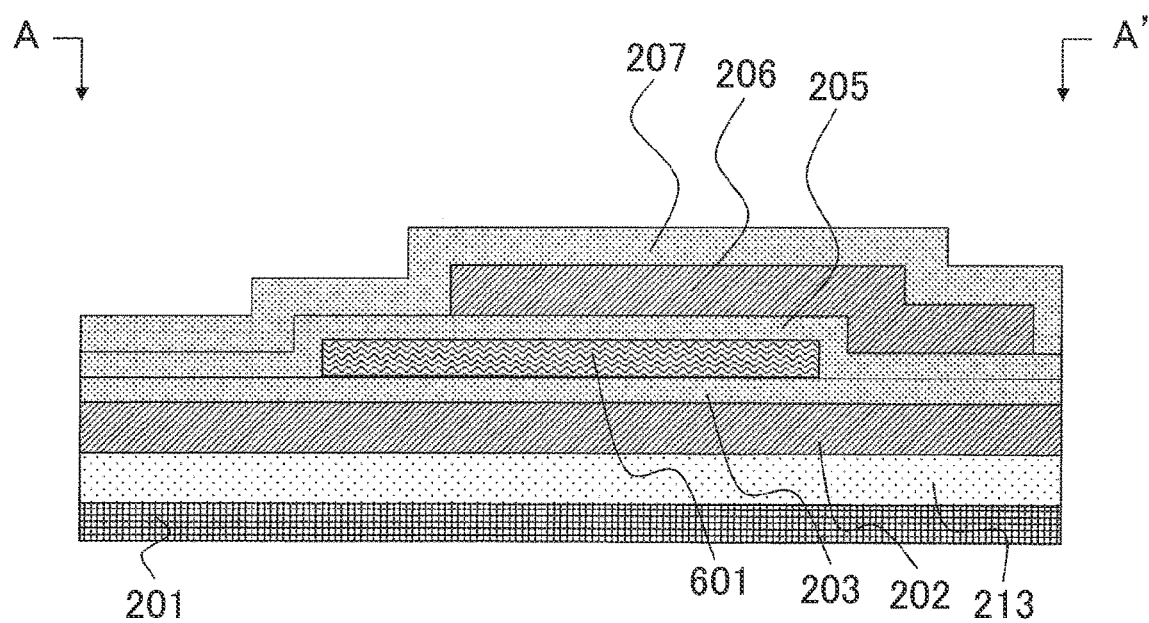
FIGS. 10 (a) and (b) are diagrams of a sixth process of the manufacturing method for the ultrasound transducer according to the first embodiment.
Figure 10:
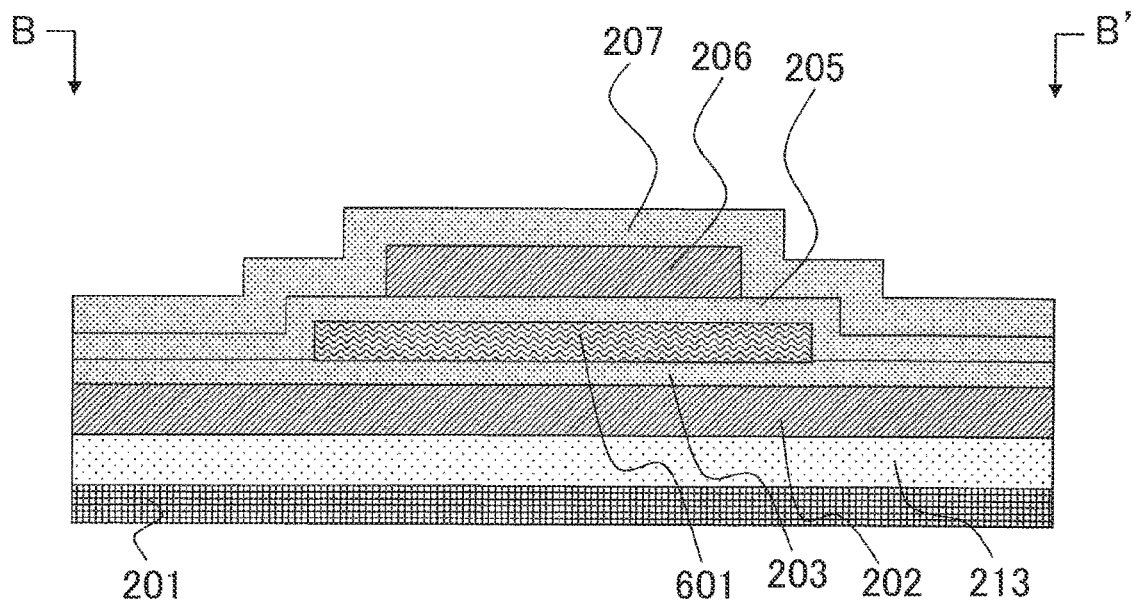
Figure 11:
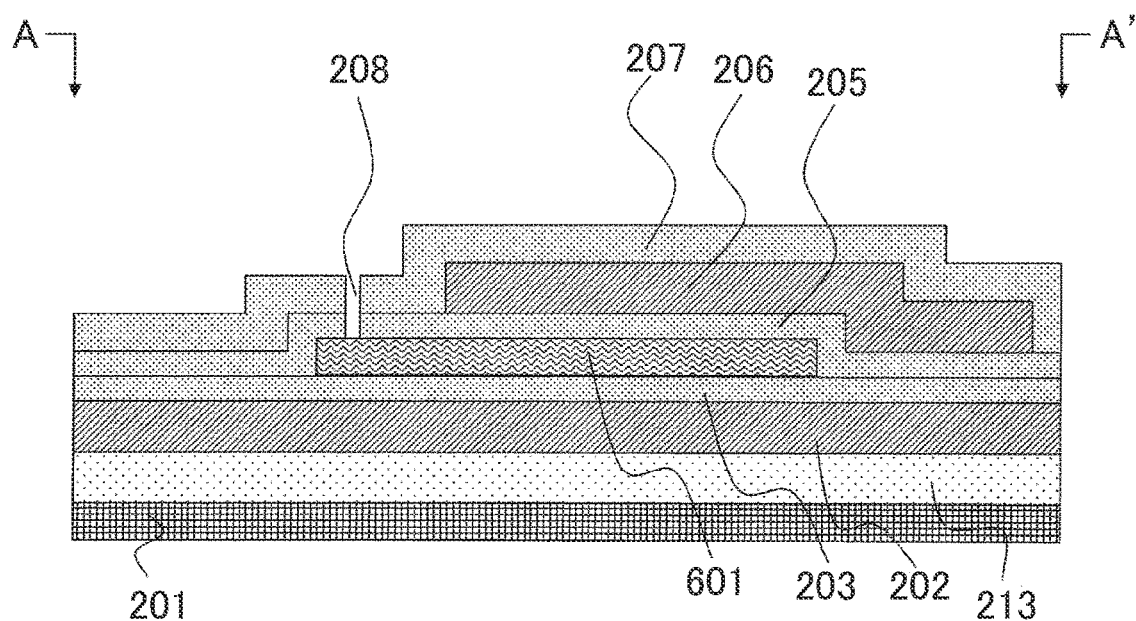
FIGS. 11 (a) and (b) are diagrams of a seventh process of the manufacturing method for the ultrasound transducer according to the first embodiment.
Figure 11:
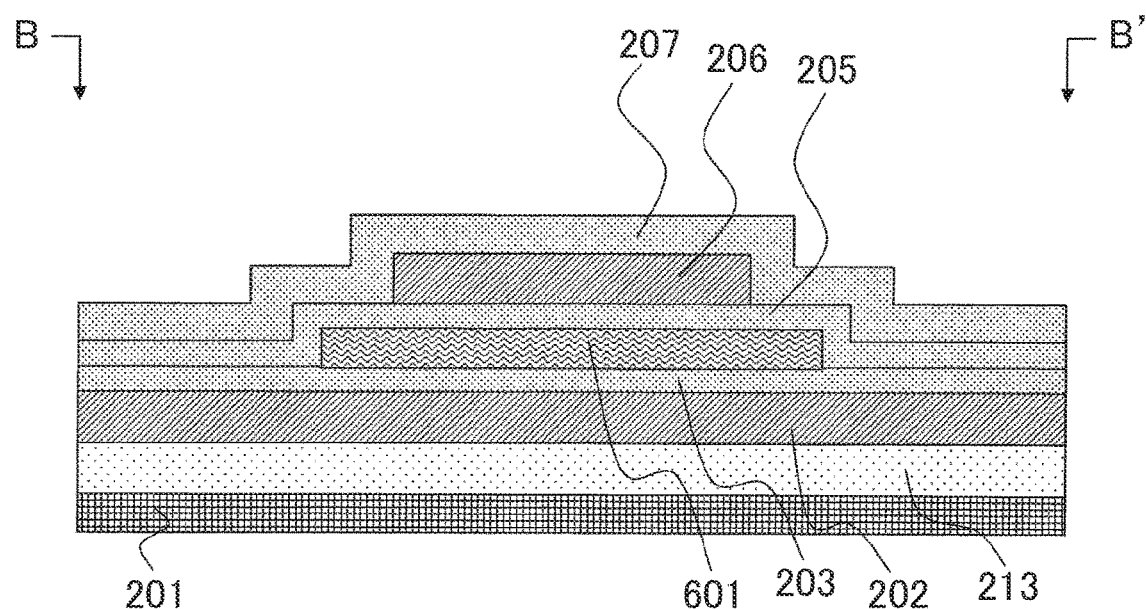

Subsequently, the insulating film 207 made of a silicon oxide film is formed in a thickness of 500 nm by plasma CVD so as to cover the insulating film 205 and the upper electrode 206 (FIGS. 10 (a) and (b)). Subsequently, on the insulating films 207 and 205, the etching hole 208 reaching the sacrificial layer 601 is formed using techniques of photolithography and dry etching (FIGS. 11 (a) and (b)).

Figure 12:
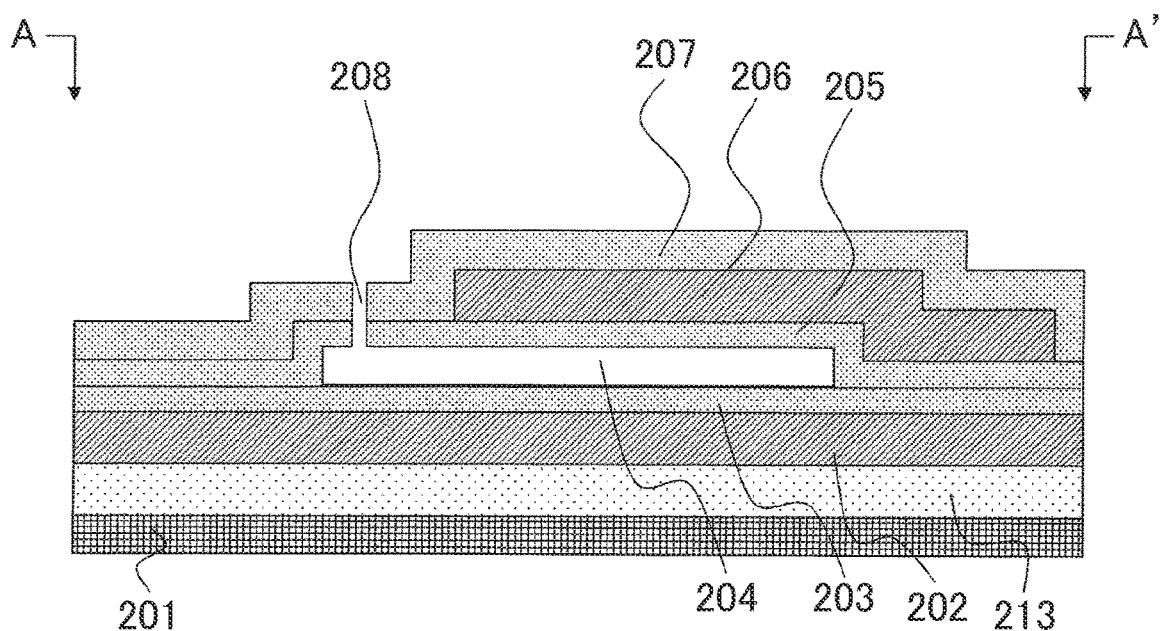
FIGS. 12 (a) and (b) are diagrams of an eighth process of the manufacturing method for the ultrasound transducer according to the first embodiment.
Figure 12:
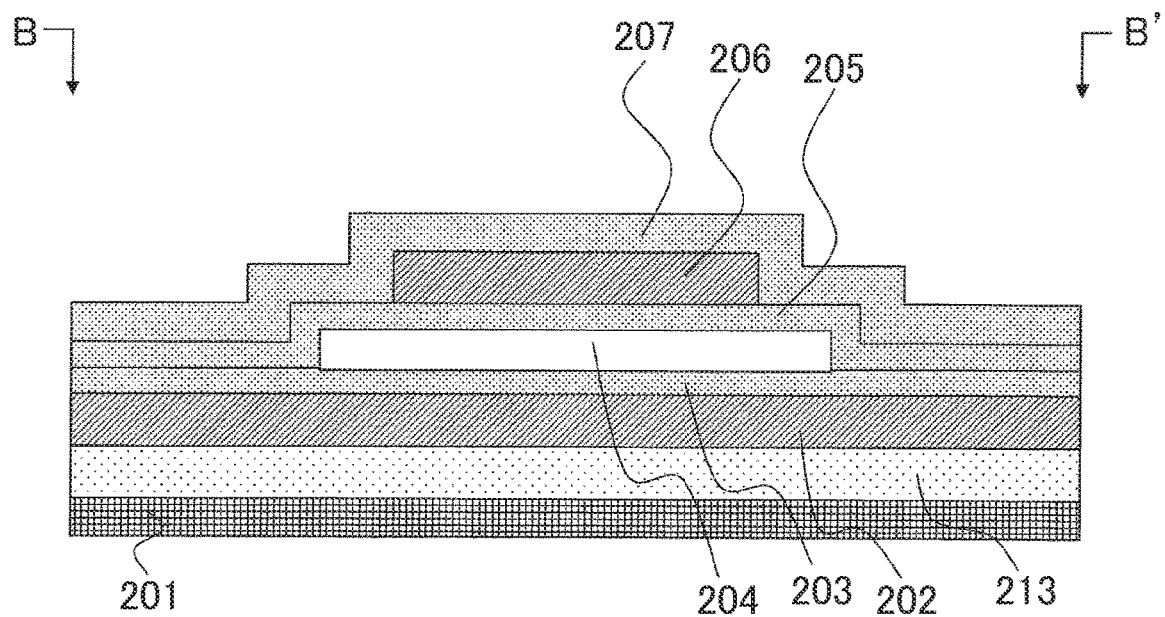

After that, the cavity 204 is formed in such a manner that the sacrificial layer 601 is isotropically etched with a xenon fluoride (XeF$_2$) gas through the etching hole 208 (FIGS. 12 (a) and (b)).

Figure 13:
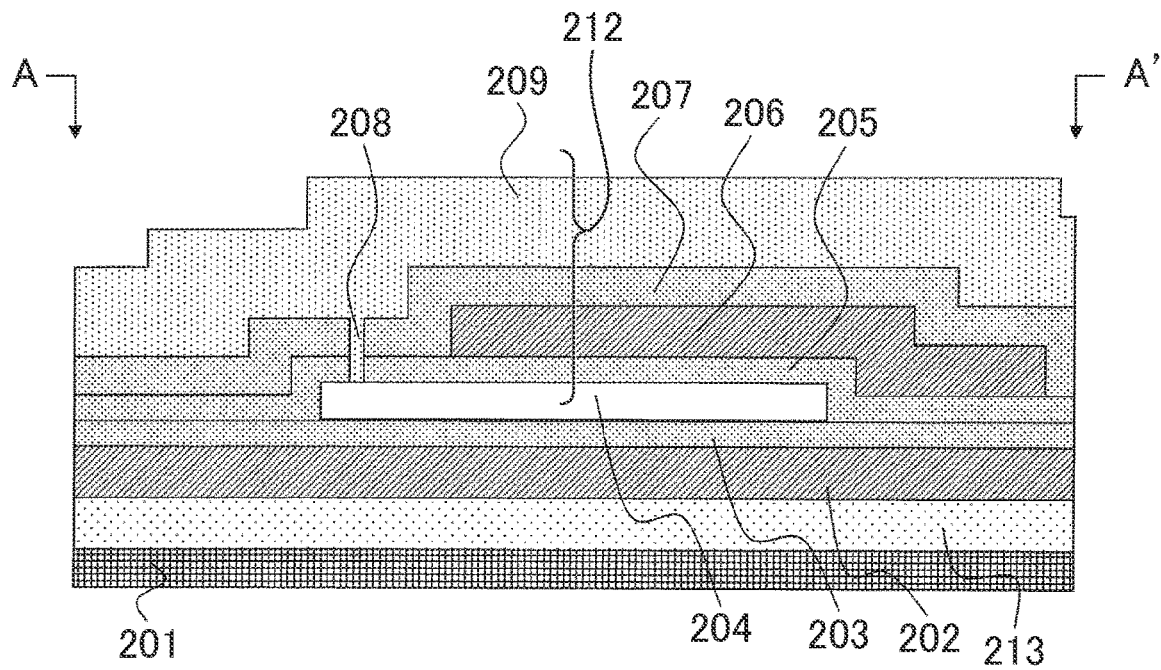
FIGS. 13 (a) and (b) are diagrams of a ninth process of the manufacturing method for the ultrasound transducer according to the first embodiment.
Figure 13:
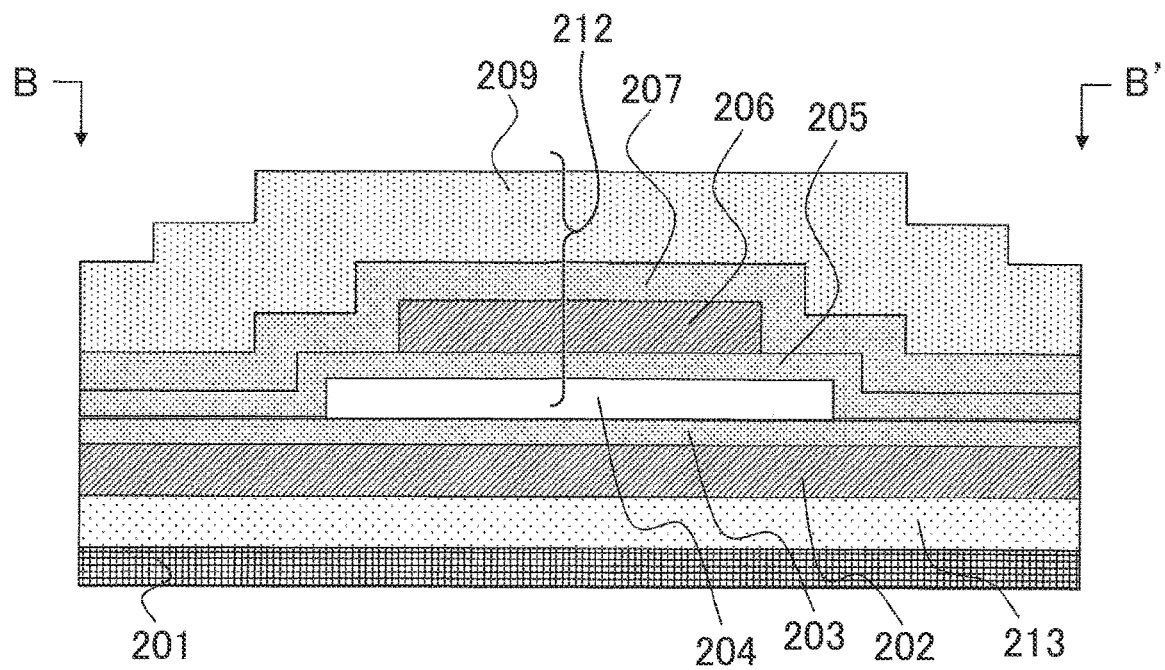

Subsequently, in order to bury the etching hole 208, the insulating film 209 made of a silicon nitride film is formed in a thickness of 800 nm by plasma CVD (FIGS. 13 (a) and (b)). By these processes, the membrane 212 formed of the insulating films 205, 207, and 209 and the upper electrode 206 is formed. Subsequently, the pad opening 211 for electrical connection to the lower electrode 202 and the pad opening 210 for electrical connection to the upper electrode 206 are formed using techniques of photolithography and dry etching. Thus, the CMUT according to the first example shown in FIGS. 3 (a) and (b) can be formed.

In FIGS. 5 to 13, only one CMUT element is shown. However, in the actual manufacturing process steps, a plurality of CMUTs or CMUT chips is simultaneously manufactured on a substrate in a diameter of a few inches or more. At this time, the stress that causes warpage (deformation) as illustrated in FIG. 4 is applied to the substrate. However, in the CMUT according to the embodiment, the warpage prevention film 213 whose stress is adjusted to other films is provided between the substrate 201 and the lower electrode 202. Accordingly, the deformation of the substrate can be effectively reduced.

Second Example

In an ultrasound transducer (CMUT) according to this example, a fourth insulating film is provided between a lower electrode (a first conductive film) 202 and a warpage prevention film 213, based on the structure of the first example. In the embodiment, for example, the warpage prevention film 213 is a silicon nitride film, and the fourth insulating film is a silicon oxide film.

Figure 14:
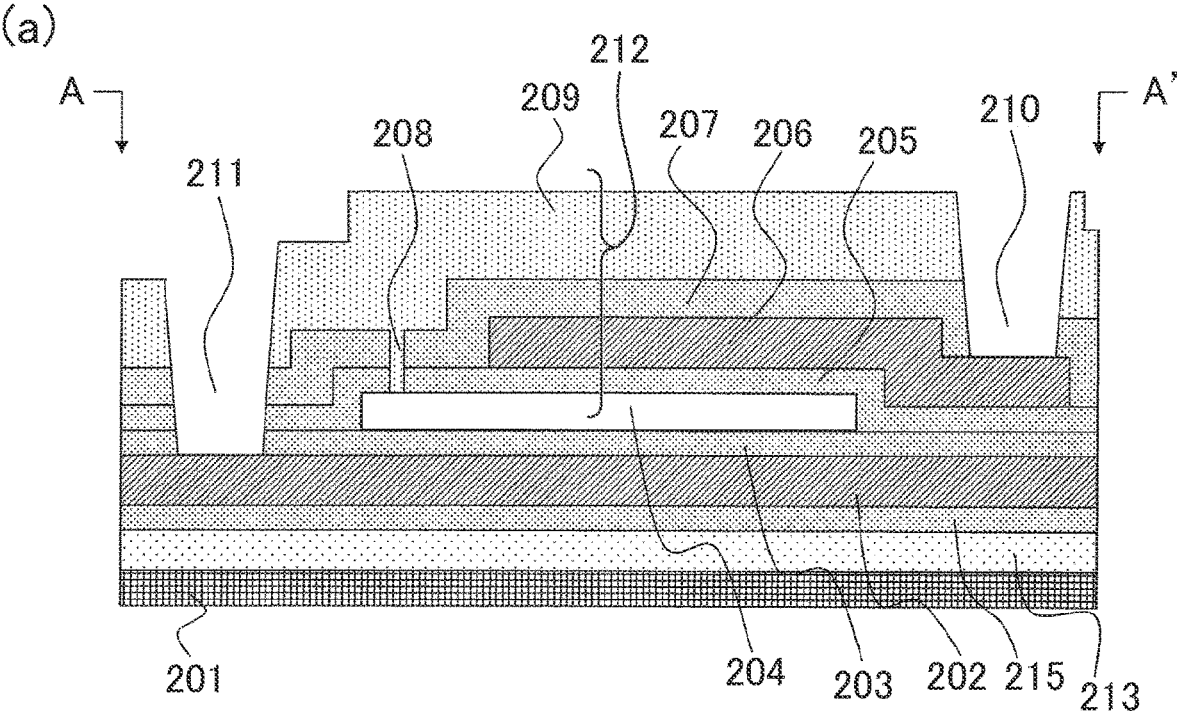
FIG. 14 show diagrams of an ultrasound transducer according to the first embodiment (a second example); (a) is a cross sectional view taken along line A-A' in FIG. 2, and (b) is a cross sectional view taken along line B-B'.
Figure 14:
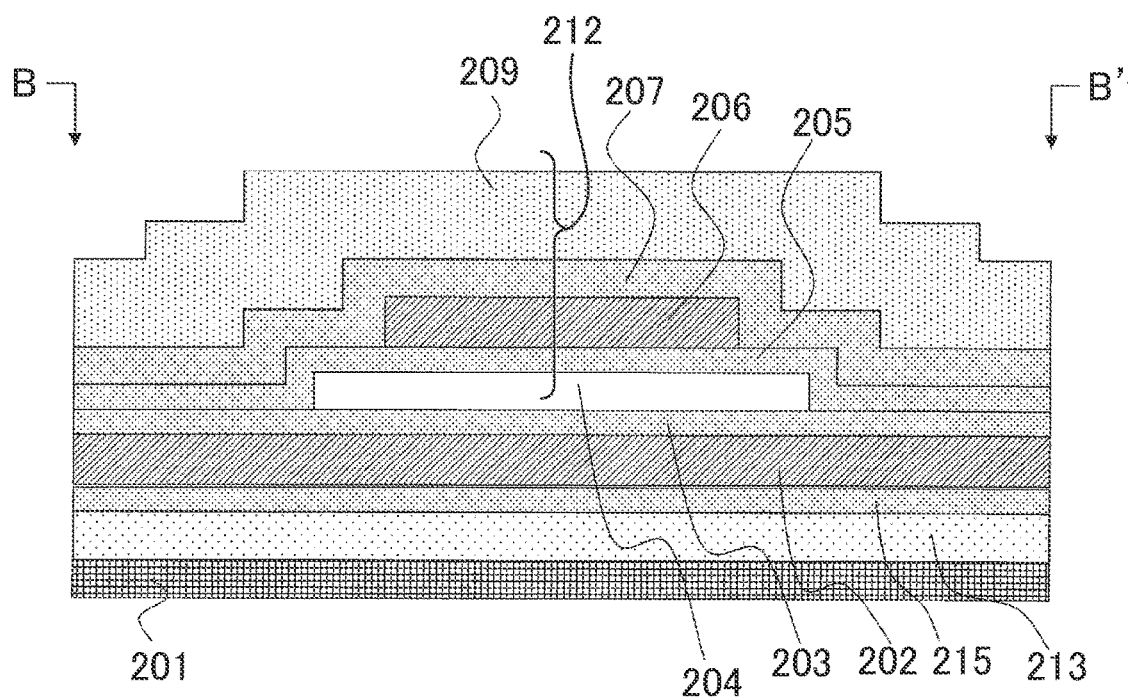

The structure of the CMUT according to the example is illustrated in FIGS. 14 (a) and (b). Also in FIG. 14, (a) is a cross section in the direction taken along line A-A' in FIG. 2, and (b) is a cross section in the direction taken along line B-B' in FIG. 2. As illustrated in the figure, the CMUT has a structure in which a silicon nitride film 213 that is a warpage prevention layer and a silicon oxide film 215 that is the fourth insulating film are stacked between a substrate 201 and a lower electrode 202. The other films are similar to those of the first example, and the description is omitted.

As described above, the silicon nitride film includes a large number of charge trapping sites in the film. Thus, leakage currents through the charge trapping sites are large, which might cause a drop in the applied voltage due to an electric current flow between the substrate and the lower electrode. In the example, a silicon oxide film having the number of charge trapping sites smaller than that in the silicon nitride film and having a small leakage current is inserted in a stack with the silicon nitride film. Thus, leakage currents can be reduced, and a drop in the voltage applied to the electrode can be reduced.

In the material characteristics of the silicon oxide film, it is difficult to provide tensile stress, and the silicon oxide film typically has compressive stress. Thus, the warping direction of the substrate is opposite to the warping direction of the silicon nitride film. However, the silicon nitride film is inserted together with the silicon oxide film, and the stress and film thickness of the silicon nitride film are adjusted, allowing the warped amount of the substrate to be controlled. A control method for the warped amount is similar to the method described in the first example using Equations (1) to (4). The warpage can be eliminated by controlling the film thicknesses of the silicon nitride film and the silicon oxide film in such a manner that the warped amount generated by the film having tensile stress and the warped amount generated by the film having compressive stress have the same absolute values.

Figure 15:
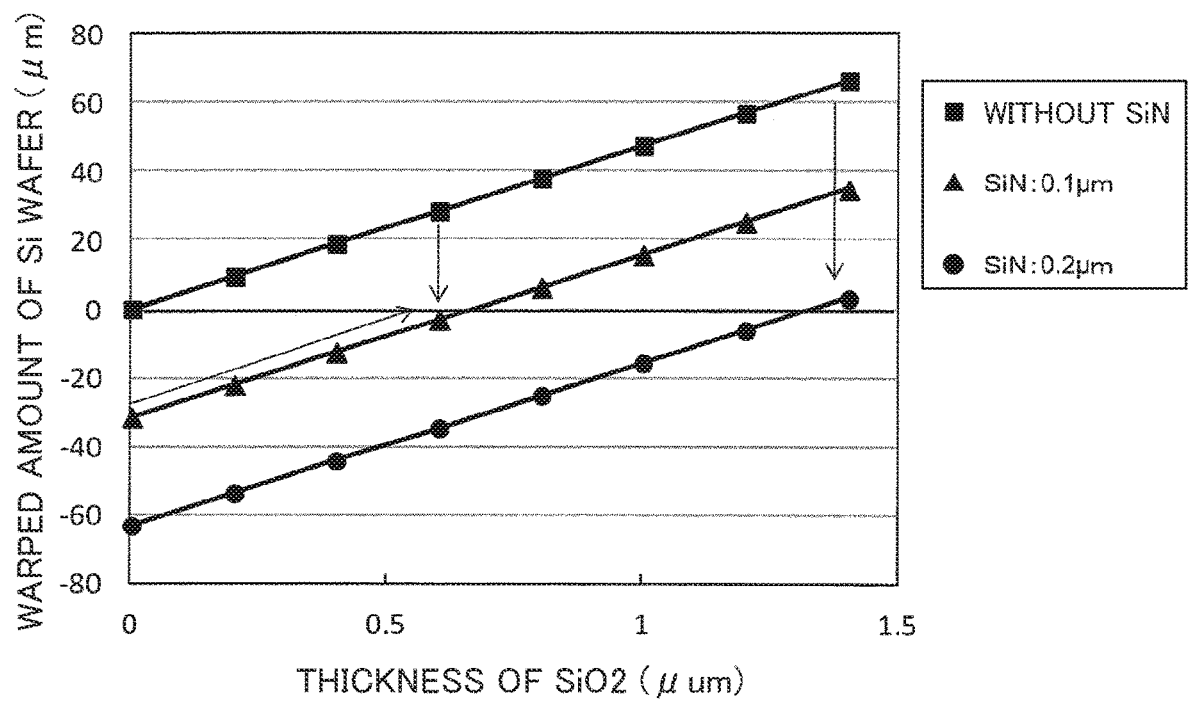
FIG. 15 is a diagram of the relationship of the film thickness of a warpage prevention layer and the warped amount in the first embodiment (the second example).

FIG. 15 shows an example of calculating warpage generated in a substrate (made of silicon) due to a silicon oxide film and a silicon nitride film. In the drawing, a graph plotted with ■ is the case where a silicon oxide film is stacked on a substrate as the thickness is changed (case 1), a graph plotted with ▲ is the case where a silicon nitride film is further stacked in a thickness of 0.1 µm on the substrate in case 1 (case 2), and a graph plotted with ● is the case where a silicon nitride film is further stacked in a thickness of 0.2 µm on the substrate in case 1 (case 3). The warped amounts are calculated from an equation in FIG. 4, where the radius r of the substrate is 100 mm, the compressive stress of the silicon oxide film is 150 MPa, and the tensile stress of the silicon nitride film is 1,000 MPa.

As apparent from the graphs in FIG. 15, the warped amount is increased almost proportional to the film thicknesses. The thicknesses of these two films are adjusted to appropriate thicknesses, allowing the warped amount to be almost zero. For example, as expressed by arrows in the graphs, in case 1 in which only the silicon oxide film is stacked, even though the substrate is warped by about +30 µm or +60 µm, the warped amount can be reduced to almost zero by forming a silicon nitride film having a tensile stress of 1,000 MPa in a thickness of 0.1 µm or 0.2 µm. In case 2, even though the substrate is warped by about −40 µm with only the silicon nitride film (the thickness of the silicon oxide film=0), the warped amount can be reduced to almost zero by forming a silicon oxide film having a compressive stress of 150 MPa in a thickness of 0.6 µm.

As described above, according to the example, the silicon oxide film 215 is inserted between the lower electrode 202 and the substrate 201. Thus, a leakage current from the lower electrode 202 to the substrate 201 can be reduced, and a drop in the applied voltage due to the leakage current can be prevented. The example is effective in the case where the amount of a drop in the applied voltage due to the leakage current is great with respect to the drive voltage.

The fourth insulating layer 215 of the example also functions as a warpage prevention layer that more effectively prevents the deformation of the substrate in a combination with the warpage prevention film 213. With the combination of the different warpage prevention layer having different stress characteristics in this manner, the warpage prevention effect can be improved. In the case where the fourth insulating layer 215 is regarded as a second warpage prevention layer, the position at which the fourth insulating layer 215 is disposed is not limited to the position shown in FIG. 14, i.e. the position between the warpage prevention film 213 and the lower electrode 202. The fourth insulating layer 215 can also be disposed between the warpage prevention film 213 and the substrate 201.

Figure 6:
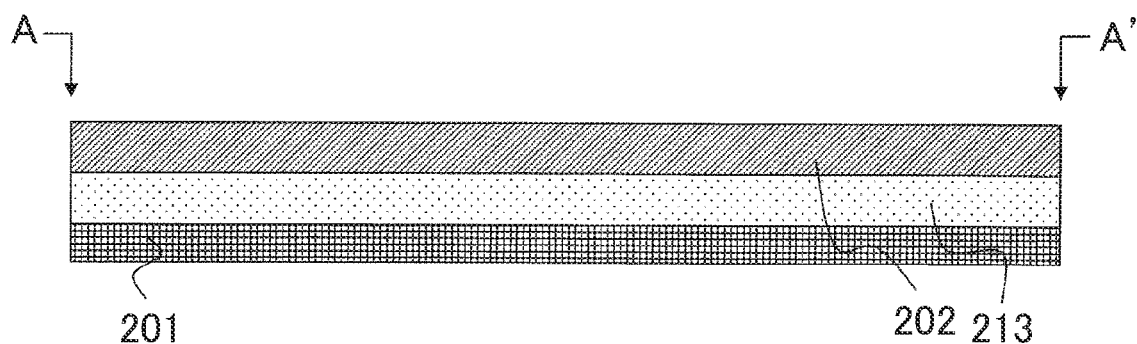
FIGS. 6 (a) and (b) are diagrams of a second process of the manufacturing method for the ultrasound transducer according to the first embodiment.
Figure 6:
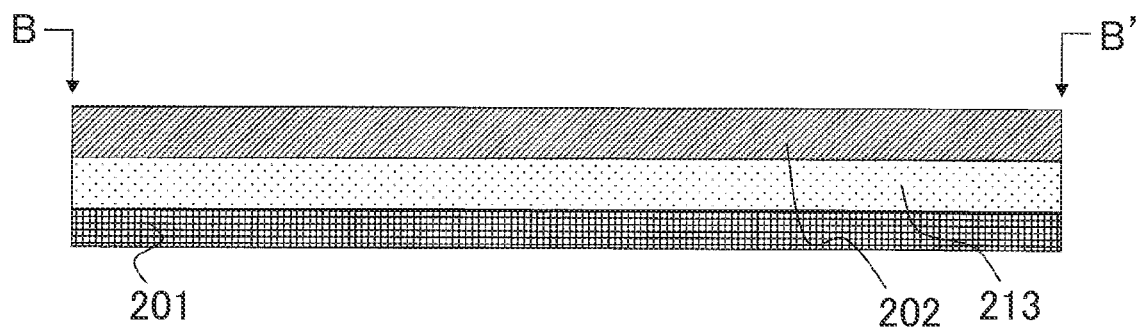

A manufacturing method for the CMUT of the example is similar to the manufacturing method for the first example except that a process of forming the insulating film 215 made of a silicon oxide film to cover the warpage prevention film 213 is added between the process of forming the warpage prevention film 213 shown in FIG. 5 and the process of forming the lower electrode 202 shown in FIG. 6. Note that, in some cases, a silicon oxide film is directly formed on the substrate, and then the process of forming the warpage prevention film 213 shown in FIG. 5 is performed.

In the description above, the case is described in which the warpage prevention film 213 and the insulating film 215 are both formed in single layers. However, various modifications are possible, including a configuration, in which any one or both of the warpage prevention film 213 and the insulating film 215 are formed in multiple layers, and a configuration, for example, in which the warpage prevention film 213 is sandwiched between a two-layer insulating film 215, and other configurations.

Third Example

In the first and the second examples, one CMUT is taken as an example and described. The embodiment of the CMUT is not limited to one CMUT element. The embodiment of the CMUT is also applicable to a CMUT chip, in which a large number of CMUT elements are arrayed.

Figure 16:
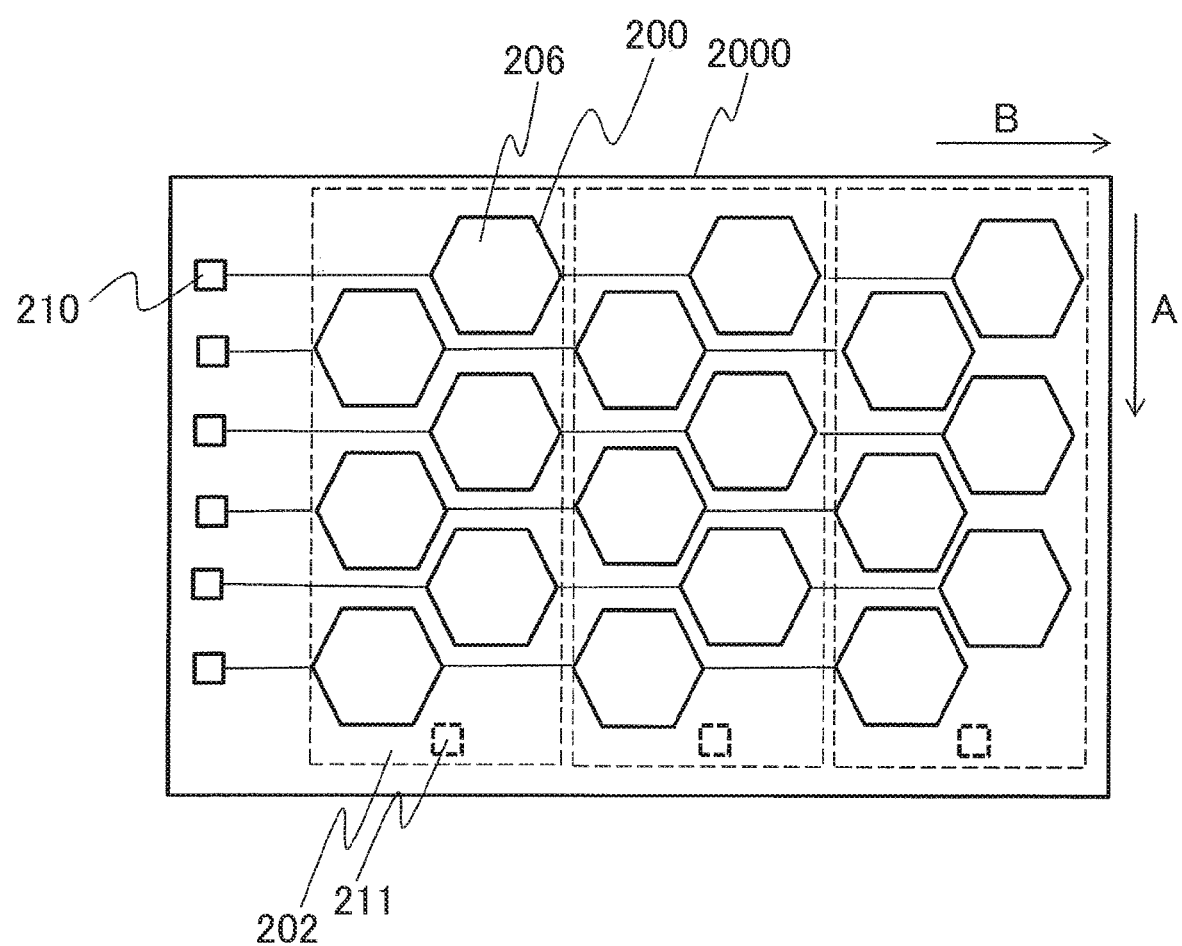
FIG. 16 is a top view of an ultrasound transducer array according to the first embodiment (a third example).

FIG. 16 is an exemplary CMUT chip to which the first embodiment is applicable. In FIG. 16, components the same as the components in FIG. 3 are designated the same reference numerals and signs, and the description is omitted. This CMUT chip 2000 has a structure, in which a large number of CMUT elements 200 are arrayed in two-dimensional directions. In FIG. 16, in the CMUT elements in the array direction indicated arrow A, a first conductive film (a lower electrode) 202 is electrically connected to a common lower electrode through a pad opening 211. In the CMUT elements in the array direction indicated by arrow B, a second conductive film (an upper electrode) 206 is electrically connected to a common upper electrode through a pad opening 210. Depending on the combinations of the upper electrode and the lower electrode carrying electric currents, the CMUT elements are individually driven to transmit and receive ultrasonic waves. Note that, in FIG. 16, an array of 18 CMUT elements 200 is simply shown. However, the number of the CMUT elements on the CMUT chip is not limited to this number. An array of a few tens to a few hundreds of the CMUT elements is also possible.

Also in this CMUT, the film configuration from the substrate to the protection insulating film is similar to the film configuration shown in FIGS. 3 or FIG. 14. The CMUT can be manufactured by a manufacturing method similar to the methods of the first and the second examples.

As the embodiment (the first embodiment) of the CMUT is described so far, according to the embodiment, the warpage of the substrate can be effectively reduced without affecting the characteristics of the CMUT. Thus, faulty chucking of the substrate or defects in processing can be solved in the manufacture of the CMUT, as well as problems, such as cracks on chips in the assembly of the CMUT on an ultrasonic device, can be solved.

Second Embodiment

As described above, in a second embodiment of the present invention, a layer (a structure) that prevents a substrate from being warped is provided on a region other than regions on the substrate on which CMUTs are provided. The region on which this structure is provided is a region that is eliminated from CMUTs after cutting the substrate into the CMUTs or CMUT chips. Thus, this feature appears in a manufacturing method for a CMUT.

In other words, a manufacturing method for a CMUT according to the embodiment is a method in which a plurality of layers including a first conductive film, a first insulating film, a second insulating film, a second conductive film, and a third insulating film is formed on a predetermined region on a substrate (in the following, referred to as a chip region) by patterning for manufacturing a plurality of ultrasound transducer arrays. The method is characterized in that in the same process as the process of the patterning, a warpage prevention layer that reduces the warpage of the substrate is formed in a predetermined pattern on an outer region on the substrate except the predetermined region (in the following, referred to as an off-chip region).

Figure 17:
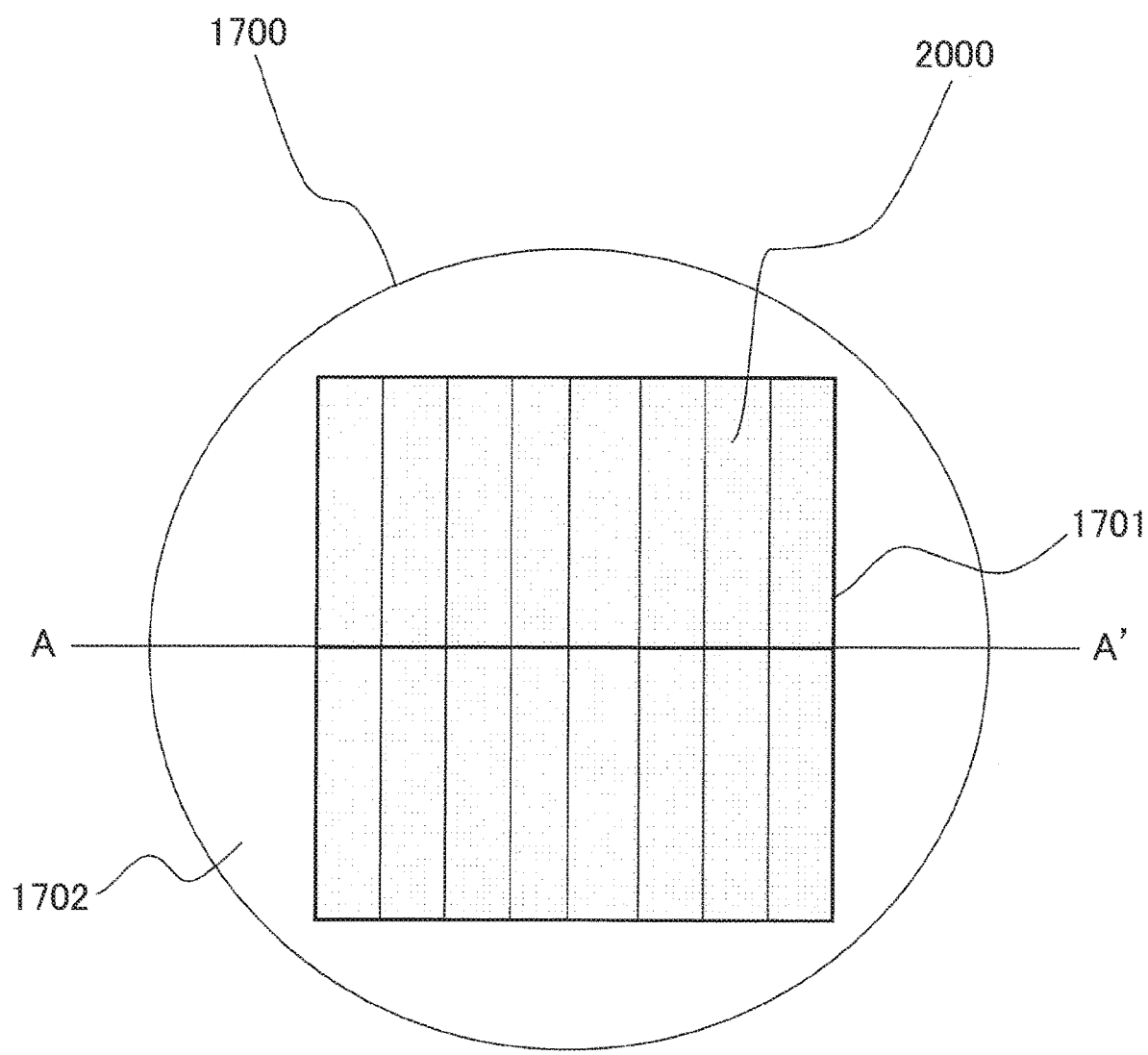
FIG. 17 is a diagram of a manufacturing method for an ultrasound transducer array according to a second embodiment when viewed from the top face of a substrate.

FIG. 17 shows an exemplary disposition of a chip region and an off-chip region on a substrate. In this exemplary disposition, a substrate 1700 has a circular shape. A chip region 1701 is a rectangular region almost inscribed in the circular substrate. In this region, a plurality of CMUT chips 2000 is formed. The CMUT chip 2000 includes an array of a large number of CMUT elements disposed in the two-dimensional directions and pad openings for supplying power to the CMUT elements as illustrated in FIG. 16, for example, and other components. The CMUTs have a film configuration as illustrated in FIG. 1 or FIG. 3. An off-chip region 1702 is a region on which a full CMUT chip 2000 is not possible to be formed when the CMUT chips 2000 are increased in the array directions. The off-chip region 1702 is the outer region of the chip region 1701.

Figure 18:
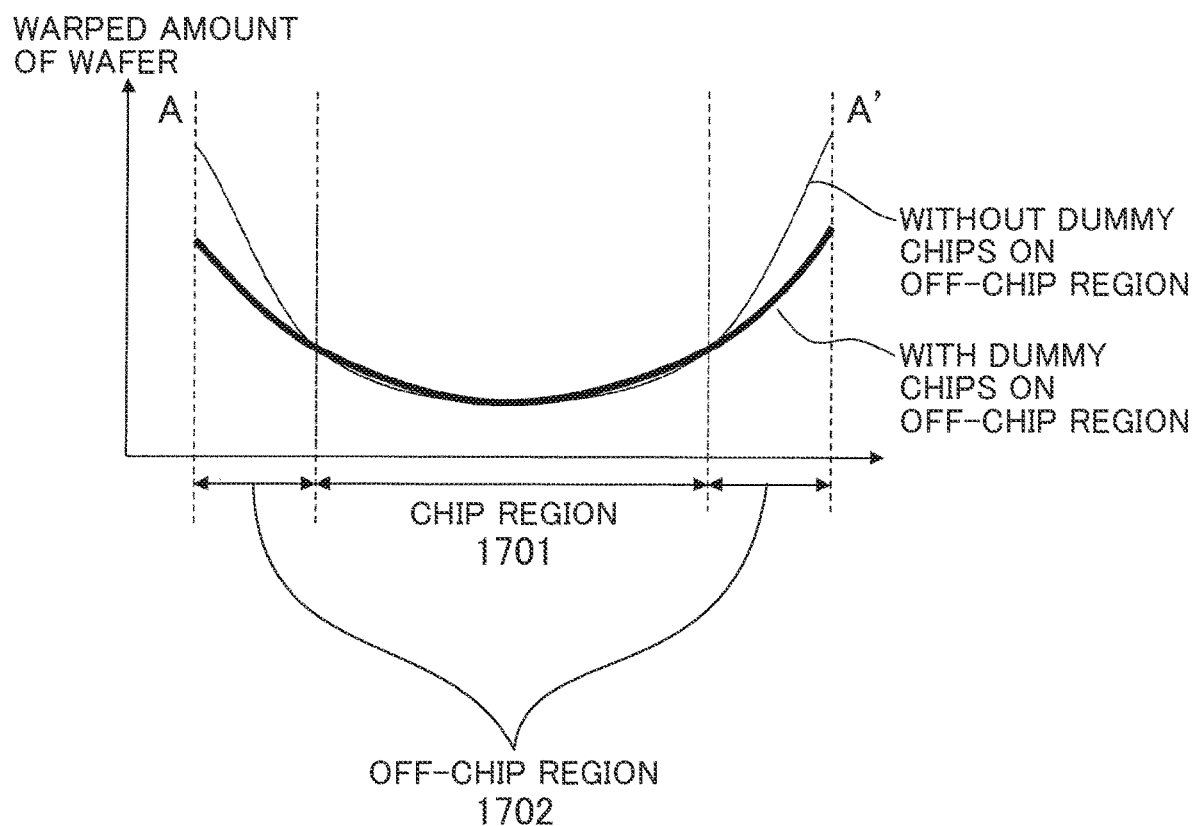
FIG. 18 is a diagram of the warpage of a substrate.

In the case where films configuring a CMUT chip are formed on the chip region 1701 of the substrate 1700, as expressed by a thin line in FIG. 18, the substrate 1700 has curvatures of warpage different on the chip region 1701 and the off-chip region 1702. On the off-chip region 1702, the warpage of the substrate is locally increased. Specifically, such local deformation of the substrate may cause faulty chucking of the substrate to the stage of the fabrication system or to cause damage on the substrate in chucking.

In the embodiment, the warpage prevention structure is provided on the off-chip region, reducing locally increasing warpage. For example, the warpage prevention structure is preferably a film stack having a layer configuration common to the layer configuration of the CMUT. For the pattern, various forms can be adopted, such as a pattern the same as the pattern of the CMUT, a plurality of patterns in different sizes, and patterns split into a plurality of sections independent of one another.

In the case where the warpage prevention structure is formed in a pattern having a layer configuration common to the layer configuration of the CMUT, the manufacture of the CMUT and the manufacture of the warpage prevention structure can be performed simultaneously in the manufacturing process steps of the CMUT described in the first example only by adding a process in which a predetermined pattern is formed on the off-chip region for forming films. Thus, since the processes of the manufacturing method are the same as the processes illustrated in FIGS. 5 to 13, the description is omitted. In the following, examples with different patterns will be described.

Fourth Example

This example is characterized in that the pattern of a chip region 1701 is used extending to an off-chip region 1702 as well.

Figure 19:
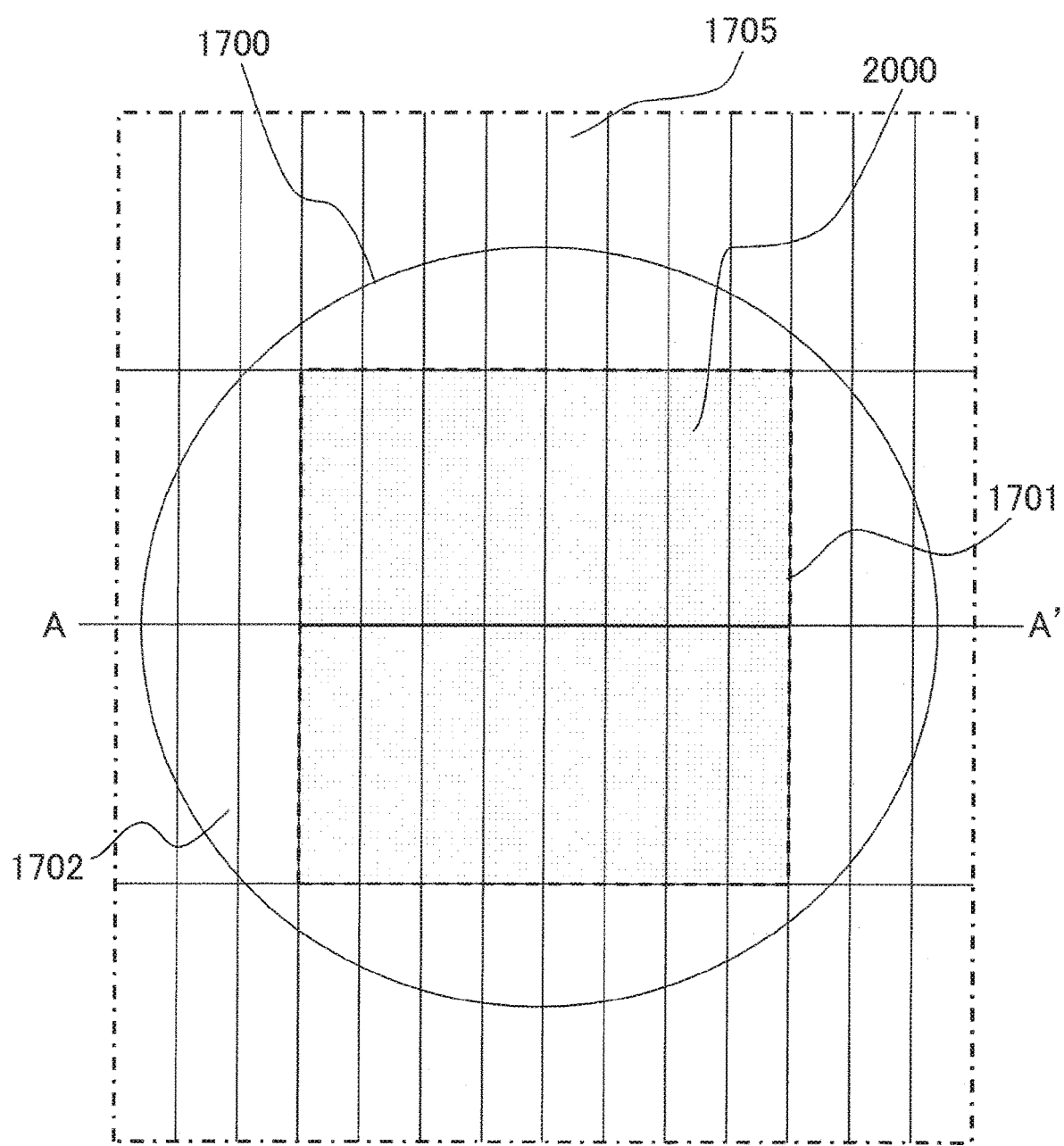
FIG. 19 is a diagram of a CMUT and an exemplary pattern of an off-chip region according to the second embodiment (a fourth example).

In the example, FIG. 19 is a top view of a substrate in the example shown in FIG. 19, on which CMUT chips are arrayed. In an example shown in FIG. 19, CMUT chips 2000 are formed in an eight-by-two array on a chip region 1701 on a substrate 1700. The other portion on the substrate 1700 is an off-chip region 1702. On the outer side of the substrate including the off-chip region 1702, a region (a dummy chip region) 1705 is provided, on which chips as dummy chips in a structure the same as the structure of the CMUT chip are prepared, although these chips are formed on the outer side of the substrate. The dummy chip region 1705 (in the drawing, a region surrounded by an alternate long and short dash line) is a region in the minimum size in which the substrate 1700 is accommodated in the region. The region includes a pattern and an array the same as those of the CMUT chip.

The chips prepared as dummy chips are chips having no substrate or chips partially lacking patterns even though the chips have a substrate. However, continuous layer structures of the chips are formed on the substrate 1700. Thus, as expressed by a thick line in FIG. 18, the warpage of the substrate 1700 has continuity between the chip region 1701 and the off-chip region 1702, allowing local deformation to be prevented.

The example can easily prevent the substrate from being deformed only by extending the pattern region of the CMUT without changing typical manufacturing process steps of the CMUT.

Fifth Example

This example is the same as the fourth example in that a dummy chip region in a structure the same as the structure of the CMUT chip is provided to prepare dummy chips. However, this example is characterized in that the dummy chip region is limited to the inside of an off-chip region 1702 of the substrate.

Figure 20:
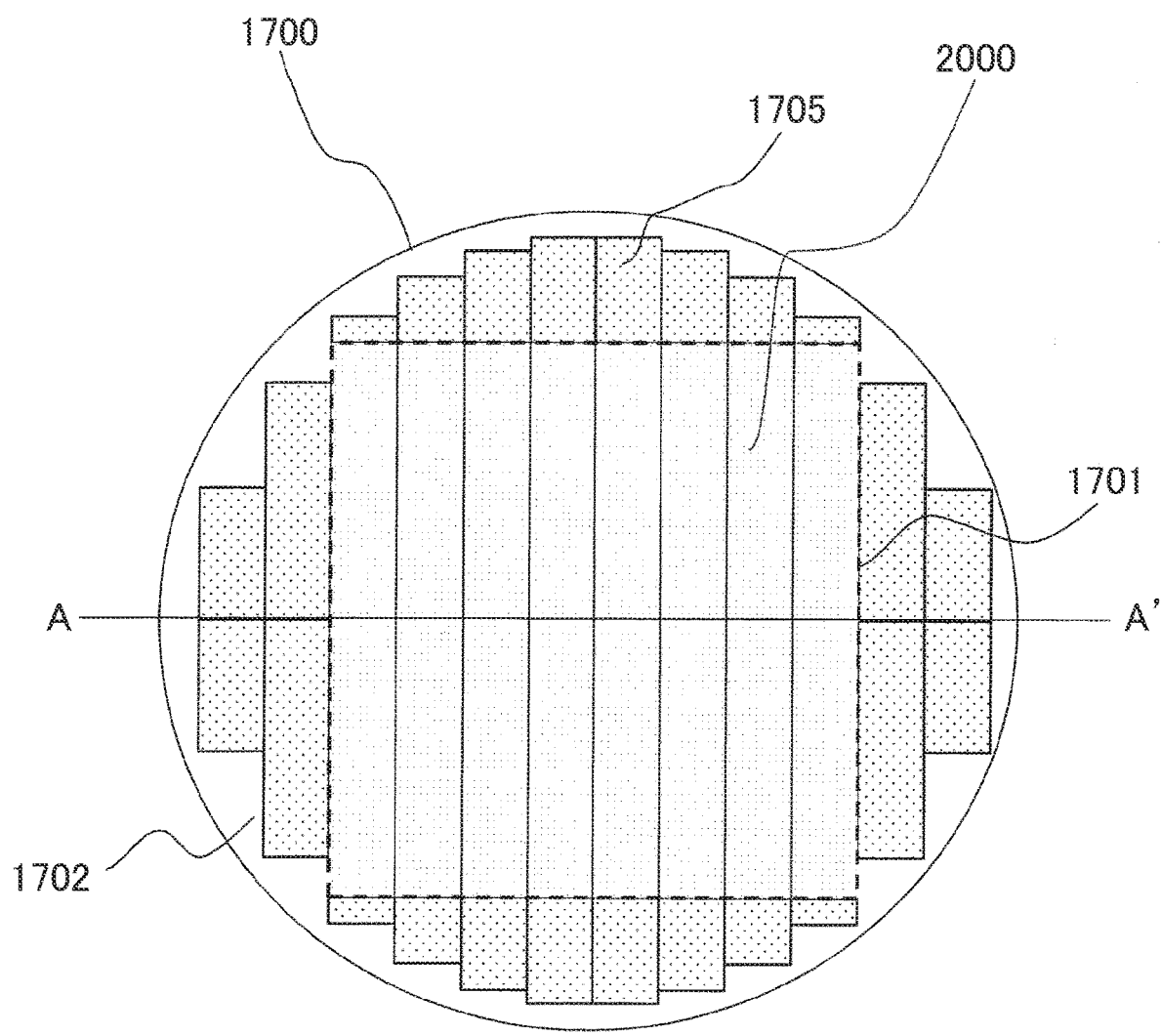
FIG. 20 is a diagram of a CMUT and an exemplary pattern of an off-chip region according to the second embodiment (a fifth example).

In other words, as illustrated in FIG. 20, a dummy chip region 1705 is provided around a chip region 1701. In the dummy chip region 1705, dummy chips in different sizes are disposed so as not to be overlapped with the end portion of a substrate 1700. In the example, in order to provide the dummy chip region on the inner side of the substrate, the sizes of the dummy chips have to be changed being matched with the shape of the off-chip region. Thus, although lithography processes in patterning the dummy chips are complicated, compares with the fourth example, advantages below can be obtained.

In other words, the dummy chip having a structure the same as the structure of the CMUT has a cavity as the same as the cavity of the CMUT. Thus, when the dummy chips are provided at locations overlapped with the end portion of the substrate as in the fourth example, the cavity of the dummy chip is likely to be overlapped with the end portion of the substrate 1700. In the manufacturing process steps of the CMUT, it is likely that a cassette conveying substrates or tweezers handling a substrate touches the end portion of the substrate to cause the membrane on the cavity to be peeled off in the midway point of the manufacturing process steps. Fragments of the peeled membrane remain on the substrate, and become foreign substances the later manufacturing process steps, causing the yields of the CMUT chips to be decreased. In the example, the dummy chip region is limited to the inner side of the substrate, and hence this problem is solved.

According to the example, the peeling of the membrane at the end portion of the substrate can be reduced. The region on which no dummy chip is arrayed is small in the off-chip region 1702. Thus, the influence on the warpage of the substrate in the region can be limited to the minimum as well.

Note that, also in the fourth and the fifth examples, as the layer configuration of the CMUT, the layer configuration of the first embodiment, i.e. the configuration, in which the warpage prevention film (the silicon nitride film) that adjusts the warpage of the substrate is inserted between the lower electrode and the substrate can be combined. Accordingly, it goes without saying that the warpage of the substrate can be further reduced.

Sixth Example

In this example, on a region of a substrate, on which no CMUT chip is disposed, an insulating film is patterned, and hence a reduction in the warpage of a wafer is achieved. In other words, a warpage prevention structure according to the example is configured of patterns in which insulating films are split into a plurality of separate blocks.

Figure 21:
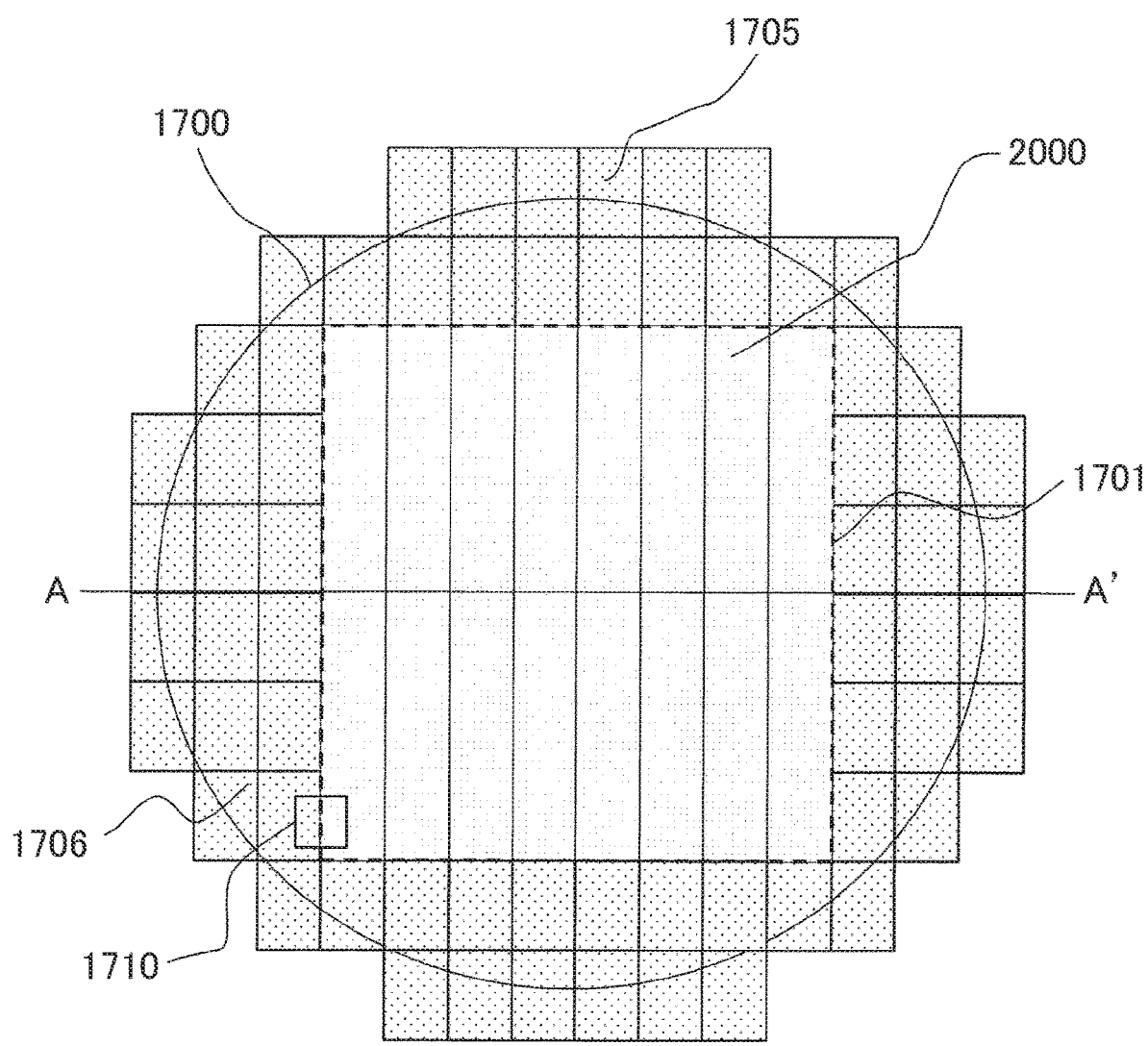
FIG. 21 is a diagram of a CMUT and an exemplary pattern of an off-chip region according to the second embodiment (a sixth example).
Figure 22:
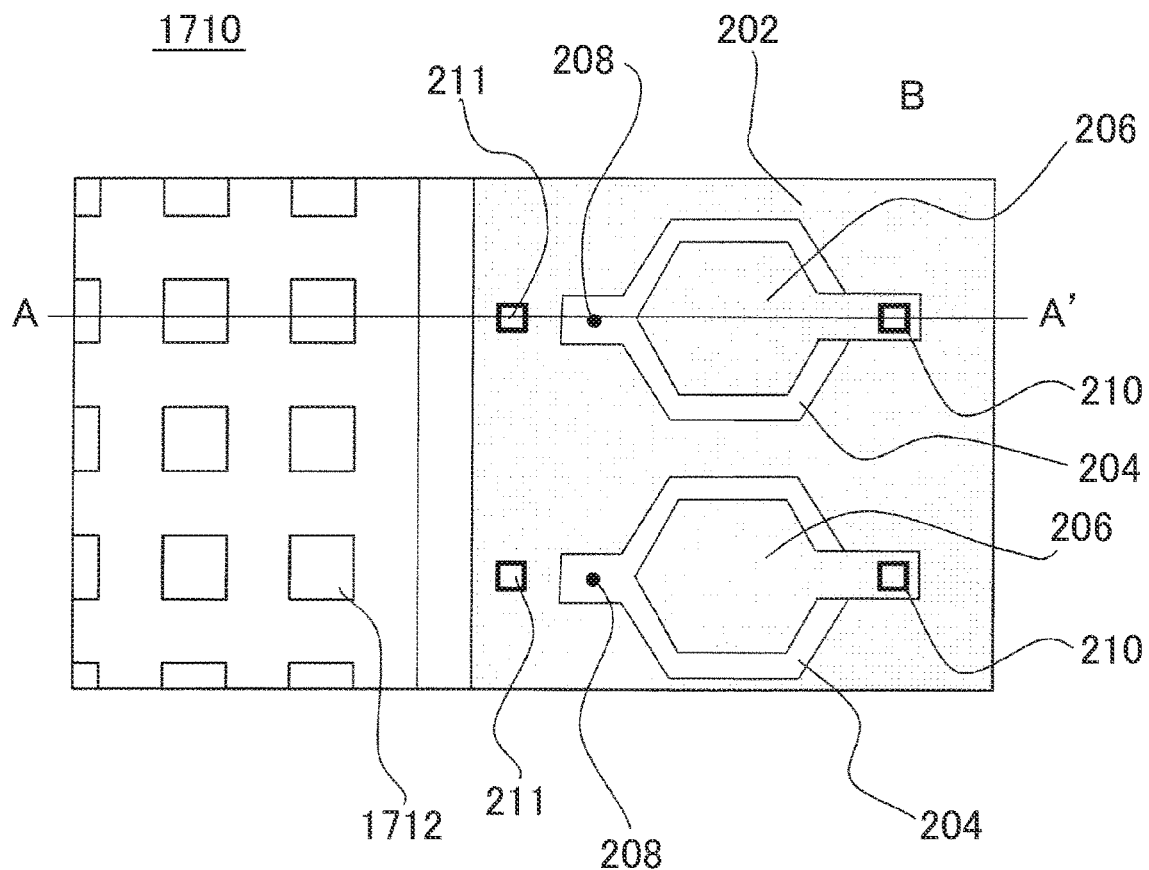
FIG. 22 is a partially enlarged top view of the pattern in FIG. 21.
Figure 23:
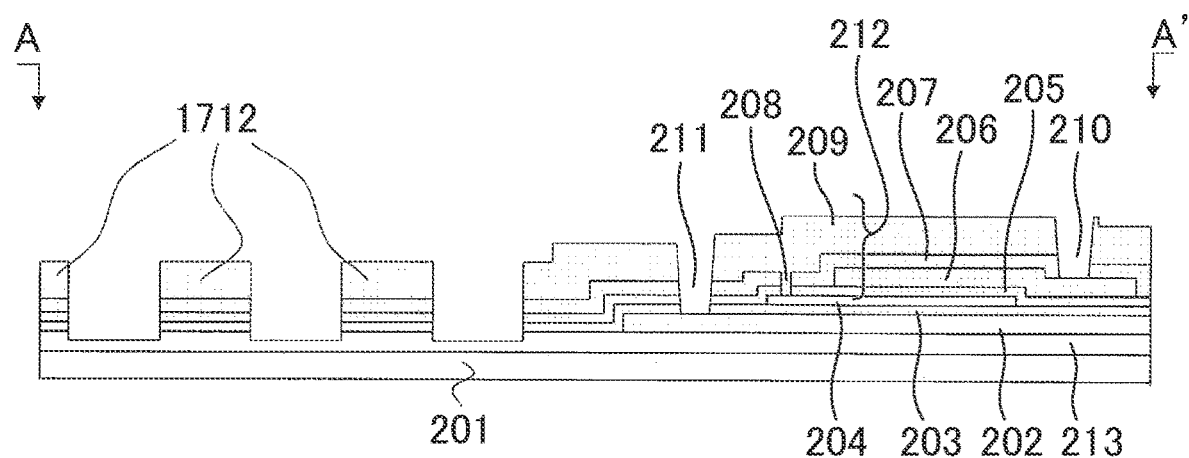
FIG. 23 is a partially enlarged cross sectional view of the pattern in FIG. 21.

FIG. 21 is a top view of a substrate on which CMUT chips are arrayed in the example. Also in FIG. 21, components the same as the components in FIG. 19 are designated the same reference numerals and signs, and the overlapping description is omitted. FIG. 22 is a top view of a part 1710 of the substrate on which the CMUT chips illustrated in FIG. 21 are arrayed. FIG. 23 is a cross sectional view of the part 1710.

As illustrated in FIG. 21, also in the example, a warpage prevention structure in a predetermined pattern is provided around a chip region 1701. A region 1705 (which is referred to as a dummy chip region here) on which a predetermined pattern is formed includes the end portion of the substrate. As illustrated in FIGS. 22 and 23, which are enlarged diagrams of the part 1710, each of dummy chips 1706 has a pattern with nearly quadrilateral blocks 1712 covered. The pattern formed of the nearly quadrilateral blocks is formed by dividing stacked insulating films by patterning.

In other words, in the manufacturing process steps of the CMUT described in the first embodiment, this pattern is prepared as below. Without forming any of the lower and upper electrodes on the off-chip region, a film stack of the first insulating film to the protection insulating film is formed (FIG. 13), and then the pattern is prepared in the subsequent process of forming the pad openings (FIG. 14). In other words, in forming the pad openings by lithography, a photomask having a nearly quadrilateral pattern is used to form the pattern on the dummy chip region by lithography. In dry etching for forming the pad openings, the pattern of the dummy chip region is simultaneously dry-etched. Thus, the structure of the divided insulating films is formed.

The insulating films on the dummy chip region are divided by patterning. Thus, the stress of the insulating films is released, allowing a reduction in the warpage of the substrate due to the stress of the insulating films on the dummy chip region. The gap between the patterns is not limited. However, the pattern dimension (the interval between the quadrilateral structures) is not greater than twice the thickness of the insulating films (the height of the quadrilateral structure). Thus, the stress of the insulating films can be more effectively released, and the warpage of the substrate can be reduced. In the drawings, the quadrilateral patterns are shown. However, a given shape can be formed, such as a circular shape and a hexagonal shape. The structures are not necessarily separate patterns. Line patterns or mesh patterns are possible.

According to the example, the pattern in a film configuration common to the film configuration of the CMUT is formed on the dummy chip region. Thus, similarly to the forgoing fourth and the fifth examples, the local deformation of the substrate can be prevented. Although the common film configurations are provided, the dummy chip has no cavity. Thus, problems can be eliminated, such as damage on the cavity due to the overlap of the cavity with the substrate and dusting, and complicated manufacturing process steps for avoiding the overlap of the cavity with the substrate. Accordingly, the warpage of the substrate can be prevented without greatly changing the general manufacturing process steps.

Note that, the insulating films to be patterned only have to include films common to the films of the CMUT. The same film configurations are not necessarily to be provided. At least films above the upper electrode, i.e. the insulating films 207 and 209 are preferably patterned.

As described above, the examples of the second embodiment of the present invention (the fourth to the sixth examples) are described. Also in these examples, as the layer configuration of the CMUT, the layer configuration of the first embodiment, i.e. the configuration, in which the silicon nitride film that adjusts the warpage of the substrate is inserted between the lower electrode and the substrate, can be combined. Thus, it goes without saying that the warpage of the substrate can be further reduced.

Third Embodiment

Lastly, an embodiment of an ultrasonic examination apparatus according to the present invention will be described.

An ultrasonic examination apparatus according to the embodiment includes: an ultrasound probe having an ultrasound transducer built in; an ultrasonic transmitter/receiver circuit that transmits an ultrasound signal to the ultrasound probe and receives an ultrasound signal detected by the ultrasound probe; and an image producing unit that produces an image using the ultrasound signal received by the ultrasonic transmitter/receiver circuit. As the ultrasound probe, an ultrasound probe is used, which includes: a substrate; a first conductive film formed on the substrate; a first insulating film and a second insulating film formed on the first conductive film; a cavity provided between the first insulating film and the second insulating film; a second insulating film formed on the second conductive film; a third insulating film covering the second conductive film; and a warpage prevention layer disposed between the substrate and the first conductive film, the warpage prevention layer preventing the substrate from being warped.

Figure 24:
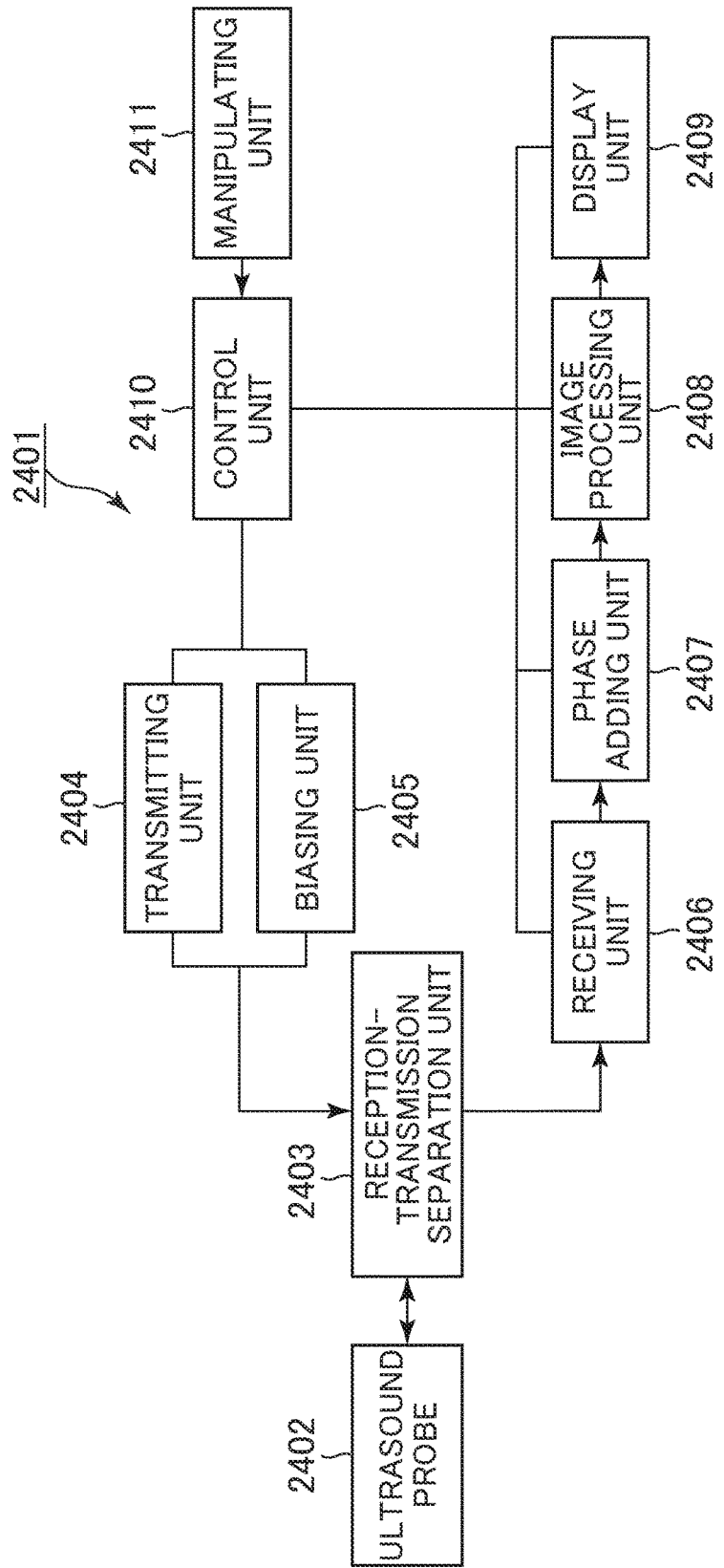
FIG. 24 is a block diagram of an overall ultrasonic examination apparatus according to an embodiment.

Referring to FIG. 24, an exemplary configuration and operation of the ultrasonic examination apparatus according to the embodiment will be described.

As illustrated in FIG. 24, the ultrasonic examination apparatus is configured of an ultrasonic examination apparatus main body 2401 and an ultrasound probe 2402. The ultrasonic examination apparatus main body 2401 is configured of a reception-transmission separation unit 2403, a transmitting unit 2404, a biasing unit 2405, a receiving unit 2406, a phase adding unit 2407, an image processing unit 2408, a display unit 2409, a control unit 2410, and a manipulating unit 2411.

The ultrasound probe 2402 is a device that is contacted with an examinee and transmits and receives ultrasonic waves with the examinee. The ultrasound probe 2402 is prepared using the CMUTs manufactured by the methods of the foregoing examples. The forms of the ultrasound probe 2402 include various forms depending on targets for examination. A basic structure includes a transducer array, a backing layer that supports the transducer array, a flexible printed board electrically connected to the transducer array, an acoustic lens disposed on the front surface of the transducer array (on the contact surface with the examinee), and other components. The transducer array is a device in which a large number of transducers are arrayed in two-dimensional directions. In the embodiment, the CMUT chip as illustrated in FIG. 16 is used.

The CMUT built in the ultrasound probe 2402 is electrically connected to the reception-transmission separation unit 2403. The reception-transmission separation unit 2403 switches and separates transmission from reception in such a manner that in the transmission of ultrasonic waves, the reception-transmission separation unit 2403 delivers a drive signal sent from the transmitting unit 2404 to the ultrasound probe 2402 and in reception, the reception-transmission separation unit 2403 delivers a received signal sent from the ultrasound probe 2402 to the receiving unit 2406.

In transmission, the transmitting unit 2404 and the biasing unit 2405 supply a drive signal to the ultrasound probe 2402, and hence ultrasonic waves are transmitted from the ultrasound probe 2402 to the examinee. In reception, reflected echo signals from the examinee are transmitted from the ultrasound probe 2402, and then the receiving unit 2406 receives the reflected echo signals outputted from the ultrasound probe 2402. Receiving unit 2406 subjects the received reflected echo signals to processing, such as analog-to-digital conversion. The phase adding unit 2407 phase-adds the received reflected echo signals, and delivers the signals to the image processing unit 2408. The image processing unit 2408 forms an examination image based on the phase-added reflected echo signals, and the display unit 2409 displays the image-processed examination image.

The control unit 2410 controls the operations of the components for transmission and reception of ultrasonic waves by the ultrasound probe 2402. The conditions and parameters for examination and instructions for control are inputted to the control unit 2410 through the manipulating unit 2411 formed of input devices, such as a track ball, keyboard, and mouse.

The ultrasonic examination apparatus according to the embodiment adopts the CMUT for the ultrasound probe. The CMUT reduces the warpage of the substrate, and secures stable operation. Thus, the operation of each of the transducers is uniform to provide stable output. Accordingly, high-quality examination images can be obtained.

Note that, the ultrasonic examination apparatus according to the embodiment is applicable to various inspection apparatuses, such as an inspection apparatus for the interior of structures, in addition to ultrasonic diagnostic apparatuses targeted for humans and animals.

LIST OF REFERENCE SIGNS 201, 1700 . . . Substrate
202 . . . Lower electrode
203 . . . First insulating film
204 . . . Cavity
205 . . . Second insulating film
206 . . . Upper electrode
207 . . . Third insulating film
208 . . . Etching hole
209 . . . Protection insulating film
210, 211 . . . Pad opening
213 . . . Warpage prevention film
215 . . . Fourth insulating film
1701 . . . Chip region
1702 . . . Off-chip region
1705 . . . Dummy chip region
1706 . . . Dummy chip
1710 . . . Part of a substrate on which CMUT chips are formed
1712 . . . Dummy chip pattern
2000 . . . CMUT chip
2401 . . . Ultrasonic examination apparatus main body
2402 . . . Ultrasound probe
2403 . . . Reception-transmission separation unit
2404 . . . Transmitting unit
2405 . . . Biasing unit
2406 . . . Receiving unit
2407 . . . Phase adding unit
2408 . . . Image processing unit
2409 . . . Display unit
2410 . . . Control unit
2411 . . . Manipulating unit

The invention claimed is:

1. A manufacturing method for an ultrasound transducer comprising:
    forming a plurality of layers including a first conductive film, a first insulating film, a second insulating film, a second conductive film, and a third insulating film on a predetermined region of a substrate by a first patterning process; and
    manufacturing a plurality of ultrasound transducers having a first film stack,
    wherein in a second patterning process that is the same as the first patterning process, a warpage prevention layer having the first film stack, that reduces warpage of the substrate, is formed in a predetermined pattern on an outer region of the substrate except the predetermined region of the substrate, and
    wherein the plurality of ultrasound transducers are only formed in the predetermined region of the substrate among the predetermined region and the outer region of the substrate.

2. The manufacturing method for an ultrasound transducer according to claim 1,
    wherein the predetermined pattern is the same pattern as a pattern of an ultrasound transducer array formed of the plurality of ultrasound transducers.

3. The manufacturing method for an ultrasound transducer according to claim 1,
    wherein the predetermined pattern is formed of a plurality of patterns in different sizes.

4. The manufacturing method for an ultrasound transducer according to claim 1,
    wherein the predetermined pattern is a pattern in which the warpage prevention layer is split into a plurality of separate blocks.

5. The manufacturing method for an ultrasound transducer according to claim 1,
    wherein the substrate has a circular shape; and
    the predetermined region is a polygon within the circle.

* * * * *